(12) United States Patent
Samuels et al.

(10) Patent No.: US 8,334,369 B2
(45) Date of Patent: Dec. 18, 2012

(54) MUTATIONS IN HUMAN UBIAD1

(75) Inventors: Mark Elliot Samuels, Westmount (CA);
Duane Guernsey, Halifax (CA);
Marie-Pierre Dube, Montreal (CA);
Andrew C. Orr, Halifax (CA)

(73) Assignee: Genome Atlantic, Halifax, Nova Scotia (CA)

( * ) Notice: Subject to any disclaimer, the term of this patent is extended or adjusted under 35 U.S.C. 154(b) by 287 days.

(21) Appl. No.: 12/524,865

(22) PCT Filed: Feb. 6, 2008

(86) PCT No.: PCT/US2008/001584
§ 371 (c)(1),
(2), (4) Date: Apr. 1, 2010

(87) PCT Pub. No.: WO2008/097585
PCT Pub. Date: Aug. 14, 2008

(65) Prior Publication Data
US 2010/0190161 A1    Jul. 29, 2010

Related U.S. Application Data

(60) Provisional application No. 60/899,726, filed on Feb. 6, 2007, provisional application No. 60/921,899, filed on Apr. 5, 2007.

(51) Int. Cl.
*C07H 21/02* (2006.01)
*C07H 21/04* (2006.01)

(52) U.S. Cl. ...................................... 536/23.1; 536/23.5

(58) Field of Classification Search .......................... None
See application file for complete search history.

(56) References Cited

FOREIGN PATENT DOCUMENTS

WO    WO 00/14251 A    3/2000

OTHER PUBLICATIONS

GenBank entry Accession NM_013319 GI 7019550 Nov. 17, 2006.*
GenBank Accession BC004468 GI 38197014 Nov. 6, 2003.*
NEB Catalog 1998/1999 pp. 121 and 284.*
GenBank Accession BT006832 GI 30582502 May 13, 2003.*
McGarvey, T.W. et al., "Isolation and characterization of the TERE1 gene, a gene down-regulated in transitional cell carcinoma of the bladder", Oncogene, vol. 20, No. 9, p. 1042-1051, Mar. 2001.
McGarvey, T.W. et al. "TERE1, a novel gene affecting growth regulation in prostate carcinoma", Prostate, vol. 54, No. 2, p. 144-155, Feb. 2003.
Orr, A. et al. "Mutations in the UBIAD1 gene, encoding a potential prenyltransferase, are causal for Schnyder crystalline corneal dystrophy", PLoS One, Pulic Library of Science, San Fransciso, CA, US, vol. 2, No. 8, p. e685, Aug. 2007.
Weiss, J.S. et al. "Mutations in the UBIAD1 gene on chromosome short arm 1, region 36, cause schnyder crystalline corneal dystrophy", Investigative Ophthalmology, Hagerstown, MD, vol. 48, No. 11, p. 5007-5012, Nov. 2007.
Yellore, V.S. et al. "Identification of mutations in UBIAD1 following exclusion of coding mutations in the chromosome 1p36 locus for Schnyder crystalline corneal dystrophy", Molecular Vision 20070924 US, vol. 13, p. 1777-1782, Sep. 2007.

* cited by examiner

*Primary Examiner* — Amanda Haney
(74) *Attorney, Agent, or Firm* — Bereskin & Parr LLP/S.E.N.C.R.L., s.r.l.; Micheline Gravelle

(57) ABSTRACT

The invention relates to polynucleotides and polypeptides which encode UBIAD1.

15 Claims, 4 Drawing Sheets

Figure 1

```
Homo        MAASQVLGEKINILSGETVKAGDRDPLGNDCPE-QDRLP--------------QRSWRQK
Pan         MAASQVLGQKINILSGETVKAGDRDPLGNDCPE-QDRLP--------------QRSWRQK
Macaca      MAASQVLGEKINILSGETVKAGDREPLGNDCPE-QDRLP--------------QRSWRQK
Mus         MAAVQAPGEKINILAGETAKVGDP--QKNEWPE-QDRLP--------------ERSWRHK
Rattus      MAAVQAPGEKINIQAGETTQVGDTDQQRNDWPE-EDRLP--------------ERSWRQK
Canis       MAASQAAG-DVNIPAGDAGRPGDREPPGPDCPE-ADRPT--------------RRSWRHK
Gallus      -MGPAELVQKISINA-ESPRGGER----NDCGAGAERGP--------------AGGWRQK
Xenopus     -MKPDDCLNNIHIETENLDEVDLTKLTGEAHSLSNGIVPPFTDKT-----FRKATSFKQK
Drosophila  MATSSQLLPNGNLSRNGKTKTEDGEEVEAVVGARAAGADAGVALTGRLTGHPSTSGTFMK
Anopheles   ------------------------------------------------------------LMK S
Homo        CASYVLALRPWSFSASLTPVALGSALAYRSHG--VLDPRLLVGCAVAVLAVHGAGNLVNT
Pan         CASYVLALRPWSFSASLTPVALGSALAYRSHG--VLDPRLLVGCAVAVLAVHGAGNLVNT
Macaca      CASYVLALRPWSFSASLTPVALGSALAYRSHG--VLDPRLLVGCAVAVLAVHGAGNLVNT
Mus         CASYVLALRPWSFSASLTPVALGSALAYRSQG--VLDPRLLLGCAVAVLAVHGAGNLVNT
Rattus      CASYVLALRPWSFSASLTPVALGSALAYRSQG--VLDPRLLLGCAVAVLAVHGAGNLVNT
Canis       CASYVLALRPWSFSASLTPVALGSALAYRAQG--GLDPRLLAGCAVAVLAVHGAGNLVNT
Gallus      CAAYVLALRPWSFSASLTPVALGSALAYRAEG--ALDPRLLVGSAVAVLAVHGAGNLVNT
Xenopus     CATYVLALRPWSFSASLTPVALGTAIAYRSGG--SLDLLLFVVCAVAVLAVHGAGNLVNT
Drosophila  LKTYLLALRPWSLSASLVPTLLGSALAYRSQWAEEFSLATFFLTAFTVVTVHCAGNVVNT
Anopheles   FKTYLSALRPWSLSASLIPTLLGTALACESGY-EHLSFFTFLCTVLTVVTVHCAGNVVNT G        G
Homo        YYDFSKGIDHKKSDDRTLVDRILEPQDVVRFGVFLYTLGCVCAACLYYLSPLKLEHLALI
Pan         YYDFSKGIDHKKSDDRTLVDRILEPQDVVRFGVFLYTLGCVCAACLYYLSPLKLEHLALI
Macaca      YYDFSKGIDHKKSDDRTLVDRILEPQDVVRFGVFLYTLGCVCAACLYCLSPLKLEHLALI
Mus         YYDFSKGIDHKKSDDRTLVDRILEPQDVVRFGVFLYTLGCVCAACLYYLSALKLEHLALI
Rattus      YYDFSKGIDHKKSDDRTLVDRILEPQDVVRFGVFLYTLGCVCAAYLYYLSTLKLEHLALI
Canis       YYDFSKGIDHKKSDDRTLVDRILEPQDVVRFGVLLYTLGCVCAAGLYSLSPLRLEHLALI
Gallus      YYDFSKGIDHKKSDDRTLVDQILEPQDVVRFGVFLYTVGCVCAAGLYAVSTLKLEHLALV
Xenopus     YYDFSKGIDHKKSDDRTLVDHILEPQDVVRFGVFLYTLGCICAACLYFISKLKLEHLALI
Drosophila  YFDFIKGIDKQKADDRTLVDHILTKDEVVSLGAILYMAGCGGFVLLAVLSPAKMEHLALI
Anopheles   YYDFVKGIDDRKADDRTLVDHILSQDEVVTLGVLLYGAGCLGFVCLVYLSPARLEHLALV I
Homo        YFGGLSGSFLYTGGIGFKYVALGDLIILITFGPLAVMFAYAIQVGSLAIFPLVYAIPLAL
Pan         YFGGLSGSFLYTGGIGFKYVALGDLIILITFGPLAVMFAYAIQVGSLAIFPLVYAIPLAL
Macaca      YFGGLSGSFLYTGGIGFKYVALGDLIILITFGPLAVMFAYAIQVGSLAIFPLVYAIPLAL
Mus         YFGGLSGSFLYTGGIGFKYVALGDLVILITFGPLAVMFAYAVQVGSLAIFPLIYAIPLAL
Rattus      YFGGLSGSFLYTGGIGFKYVALGDLVILITFGPLAVMFAYAVQVGSLAIFPLVYAIPLAL
Canis       YFGGLSGSFLYTGGIGFKYVALGDLVILITFGPLAVMFAYAVQVGSLAVFPLVYAIPLAL
Gallus      YFGGLSSSFLYTGGIGFKYVALGDVVILITFGPLAVMFAHAVQVGYLSVSPLIYAVPLAL
Xenopus     YFGGLSSSFLYTGGIGFKYVALGDLVILITFGPLAVMFAHAVQVGYLAVTPLIYAVPLAL
Drosophila  YFGGLSSSFLYTGGIGFKYIALGDLVILILFGPISVLFAFMSQTGHLDWTTMGYAIPLAL
Anopheles   FFGGLSSSFLYTGGFGLKYIALGDVLVLVIFGPISVLFSYMAQTGRYEWATIFYAIPLAL
```

Figure 1 (cont'd)

```
                         s
Homo        STEAILHSNNTRDMESDREAGIVTLAILIGPTFSYILYNTLLFLPYLVFSILATHCTISL
Pan         STEAILHSNNTRDMESDREAGIVTLAILIGPTFSYILYNTLLFLPYLVFSILATHCTISL
Macaca      STEAILHSNNTRDMESDREAGIVTLAILIGPTFSYILYNTLLFLPYLVFSILATHCTISL
Mus         STEAILHSNNTRDMESDREAGIVTLAILIGPTFSYVLYNTLLFVPYLIFTILATHCSISL
Rattus      STEAILHSNNTRDMESDREAGIVTLAILIGPTLSYILYNTLLFLPYLIFTILATHCSISL
Canis       STEAILHSNNTRDMESDREAGIVTLAILIGPTLSYMLYNTLLFLPYLIFSILATRCSISL
Gallus      STEAILHSNNTRDMESDQQAGIVTLAILIGPAFSYVLYTVLLFLPYLIFCVLATRYTISM
Xenopus     STEAILHSNNTRDMESDRQAGIVTLAILVGPMFSYMLYNLLVFLPYLIFSILATRYTISM
Drosophila  NTEAILHSNNTRDADNDRRAGIVTLAILIGRTASHVLYAMLLFAPYSLFFIFGLKYSLWF
Anopheles   NTEAILHSNNTRDAESDKRVGIVTLAILIGRTGSYILYGVLLFTPYVIFVVLGMKYSALF Homo        ALPLLTIPMAFSLERQFRS-QAFNKLPQRTAKLNLLLGLFYVFGIILAPAGSLPKI---
Pan         ALPLLTIPMAFSLERQFRS-QAFNKLPQRTAKLNLLLGLFYVFGIILAPAGSLPKI---
Macaca      ALPLLTIPMAFSLERQFRS-QAFNKLPQRTAKLNLLLGLFYVFGIILAPAGSLPKL---
Mus         ALPLLTIPMAFSLERQFRS-QAFNKLPQRTAKLNLLLGLFYVFGIILAPAGSLPRL---
Rattus      ALPLLTSPMAFSLERQFRS-QAFNKLPQRTAKLNLLLGLFYVFGIILAPAGSLPRL---
Canis       ALPLLTIPMAFSLERQFRS-QTFNKLPQRTAKLNLLLGLFYVFGIILAPAGSLPKL---
Gallus      ALPLLTIPMAFSLERQFRS-QNFNKIPQRTAKLNLLLGLFYVFGIMLAPAGALPKL---
Xenopus     ALPLLTIPLAFSLERQFRS-QNFNKIPQRTAKLNLLVGLFYVFGIVLAPAGSLP-----
Drosophila  LLPLVTLPQAFQIEKRFRNECTMHLVPRQTAKLNFFFGILYVVACCCAHQLPTFGLRRN
Anopheles   LLPMVTFKQAFALERQFRNESTMQMVPRQTAKLNLFFGILYVVACFGAPQLP-FITRK-
```

Figure 3
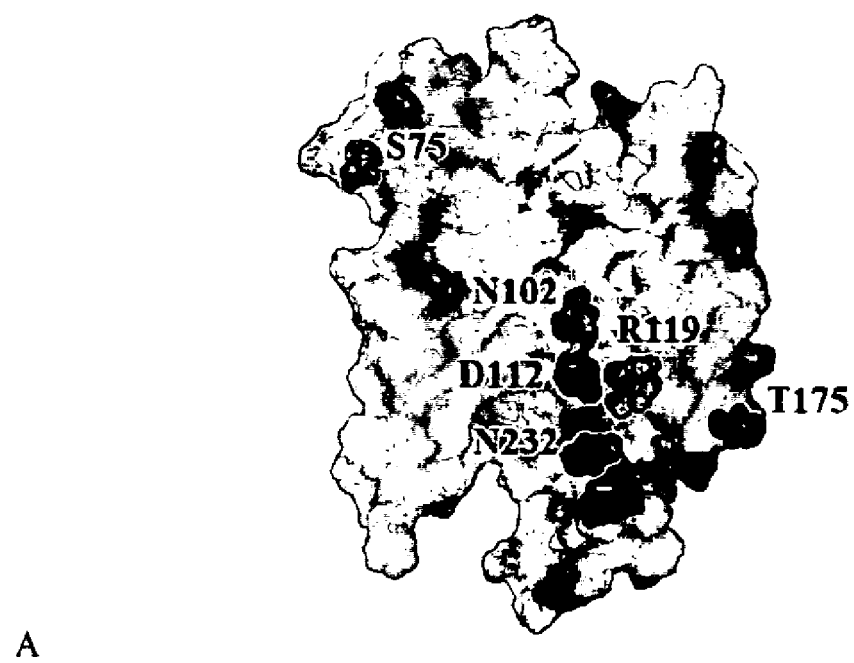
A
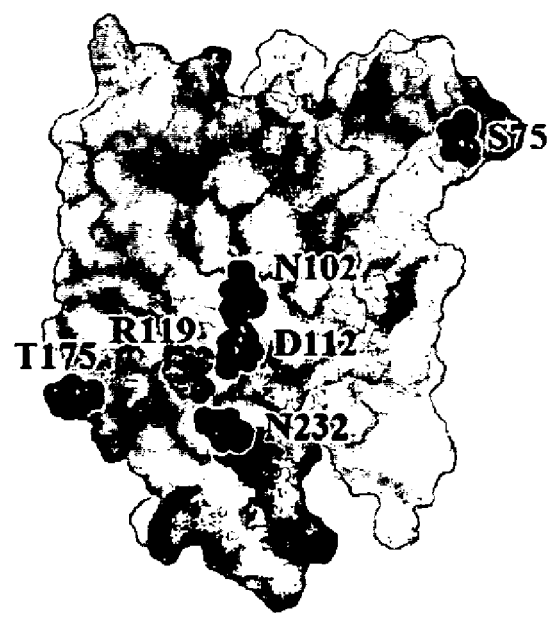
B

SEQUENCE LISTING

<160> NUMBER OF SEQ ID NOS: 122

<210> SEQ ID NO 1
<211> LENGTH: 1517
<212> TYPE: DNA
<213> ORGANISM: Homo sapiens

<400> SEQUENCE: 1

```
ggccgcgaat tcggcacgag cggcgcacaa gatggcggct ctggcggcct aaagaaggcc      60
gcggccgcgg ctcagccgtg ggctctaacg cggggctggg ggccggagac agacttccag     120
gtgacgggta gtagggggcgg cgccgcttgg cctcgtgggg tgtaagaccc acttgctgtt    180
gcccccggac cttgccgcca caccagcccct gtcctggggc ggaaccgaag gaaggtcggg    240
ccctgctgcc ccgccccgtc cttcctcctt cccgggcggt cactgtgcgt ggctcacttt    300
tagagtttac ttcaaccacg tggagcttcc atggcggcct ctcaggtcct gggggagaag    360
attaacatcc tgtcgggaga gactgtcaaa gctggggaca gggacccgct ggggaacgac    420
tgtcccgagc aagataggct cccccagcgc tcctggaggc agaagtgtgc ctcctacgtg    480
ttggccctga ggcctggag cttcagtgcc tcactcacac cggtggccct gggcagtgcc    540
cttgcctaca gatcccacgg tgtcctggat cccaggctct tggtgggttg tgccgtggct    600
gtcctggctg tgcacggggc cggtaatttg gtcagcactt actatgactt ttccaagggc    660
attgaccaca aaaagagtga tgacaggaca cttgtggacc gaatcttgga gccgcaggat    720
gtcgtccggt tcggagtctt cctctacacg ttgggctgcg tctgtgccgc ttgcctctac    780
tacctgtccc ctctgaaact ggagcacttg gctcttatct actttggagg cctgtctgcc    840
tcctttctct acacaggagg aattggattc aagtacgtgg ctctgggaga cctcatcatc    900
ctcatcactt ttggcccgct ggctgtgatg ttcgcctacg ccatccaggt ggggtccctg    960
gccatcttcc cactggtcta tgccatcccc ctcgccctca gcaccgaggc cattctccat   1020
tccaacaaca cagggacat ggagtccgac cgggaggctg tatcgtcac gctggccatc     1080 ctcatcggcc ccacgttctc ctacattctc tacaacacac tgctcttcct gccctacctg   1140
gtcttcagca tcctggccac acactgcacc atcagcctgg cactcccct gcttaccatt   1200 cccatggcct tctcccttga gagacagttt cgaagccagg ccttcaacaa actgccccag  1260
```

```
aggactgcca agctcaacct cctgctggga cttttctatg tctttggcat cattctggca    1320
ccagcaggca gtctgcccaa aatttaaggg gacaagtagc tccccccacg acatgtctcc    1380
ctttcttaga atatattaaa gtcagagtct ctgaggaagg aatgtgattt ggcagtcagg    1440
gtactaagca tgggtgggaa ctcctgcctt ataaaaattg ttttgtgttc ttaaagataa    1500
aaaaaaaaaa aaaaaaa                                                   1517

<210> SEQ ID NO 2
<211> LENGTH: 338
<212> TYPE: PRT
<213> ORGANISM: Homo sapiens

<400> SEQUENCE: 2

Met Ala Ala Ser Gln Val Leu Gly Glu Lys Ile Asn Ile Leu Ser Gly
1               5                   10                  15

Glu Thr Val Lys Ala Gly Asp Arg Asp Pro Leu Gly Asn Asp Cys Pro
            20                  25                  30

Glu Gln Asp Arg Leu Pro Gln Arg Ser Trp Arg Gln Lys Cys Ala Ser
        35                  40                  45

Tyr Val Leu Ala Leu Arg Pro Trp Ser Phe Ser Ala Ser Leu Thr Pro
    50                  55                  60

Val Ala Leu Gly Ser Ala Leu Ala Tyr Arg Ser His Gly Val Leu Asp
65                  70                  75                  80

Pro Arg Leu Leu Val Gly Cys Ala Val Ala Val Leu Ala Val His Gly
                85                  90                  95

Ala Gly Asn Leu Val Ser Thr Tyr Tyr Asp Phe Ser Lys Gly Ile Asp
            100                 105                 110

His Lys Lys Ser Asp Asp Arg Thr Leu Val Asp Arg Ile Leu Glu Pro
        115                 120                 125

Gln Asp Val Val Arg Phe Gly Val Phe Leu Tyr Thr Leu Gly Cys Val
    130                 135                 140

Cys Ala Ala Cys Leu Tyr Tyr Leu Ser Pro Leu Lys Leu Glu His Leu
145                 150                 155                 160

Ala Leu Ile Tyr Phe Gly Gly Leu Ser Gly Ser Phe Leu Tyr Thr Gly
                165                 170                 175

Gly Ile Gly Phe Lys Tyr Val Ala Leu Gly Asp Leu Ile Ile Leu Ile
            180                 185                 190

Thr Phe Gly Pro Leu Ala Val Met Phe Ala Tyr Ala Ile Gln Val Gly
        195                 200                 205

Ser Leu Ala Ile Phe Pro Leu Val Tyr Ala Ile Pro Leu Ala Leu Ser
    210                 215                 220

Thr Glu Ala Ile Leu His Ser Asn Asn Thr Arg Asp Met Glu Ser Asp
225                 230                 235                 240

Arg Glu Ala Gly Ile Val Thr Leu Ala Ile Leu Ile Gly Pro Thr Phe
                245                 250                 255

Ser Tyr Ile Leu Tyr Asn Thr Leu Leu Phe Leu Pro Tyr Leu Val Phe
            260                 265                 270

Ser Ile Leu Ala Thr His Cys Thr Ile Ser Leu Ala Leu Pro Leu Leu
        275                 280                 285

Thr Ile Pro Met Ala Phe Ser Leu Glu Arg Gln Phe Arg Ser Gln Ala
    290                 295                 300

Phe Asn Lys Leu Pro Gln Arg Thr Ala Lys Leu Asn Leu Leu Gly
305                 310                 315                 320

Leu Phe Tyr Val Phe Gly Ile Ile Leu Ala Pro Ala Gly Ser Leu Pro
                325                 330                 335
```

Lys Ile

<210> SEQ ID NO 3
<211> LENGTH: 1517
<212> TYPE: DNA
<213> ORGANISM: Homo sapiens

<400> SEQUENCE: 3

```
ggccgcgaat tcggcacgag cggcgcacaa gatggcggct ctggcggcct aaagaaggcc      60
gcggccgcgg ctcagccgtg ggctctaacg cggggctggg ggccggagac agacttccag     120
gtgacgggta gtaggggcgg cgccgcttgg cctcgtgggg tgtaagaccc acttgctgtt     180
gcccccggac cttgccgcca caccagccct gtcctggggc ggaaccgaag gaaggtcggg     240
ccctgctgcc ccgccccgtc cttcctcctt cccggccggt cactgtgcgt ggctcacttt     300
tagagtttac ttcaaccacg tggagcttcc atggcggcct ctcaggtcct ggggagaag      360
attaacatcc tgtcgggaga gactgtcaaa gctggggaca gggacccgct ggggaacgac     420
tgtcccgagc aagataggct cccccagcgc tcctggaggc agaagtgtgc ctcctacgtg     480
ttggccctga ggccctggag cttcagtgcc tcactcacac cggtggccct gggcagtgcc     540
cttgcctaca gatcccacgg tgtcctggat cccaggctct tggtgggttg tgccgtggct     600
gtcctggctg tgcacgggc cggtaatttg gtcaacactt actatgactt ttccaagggc      660
attggccaca aaagagtga tgacaggaca cttgtggacc gaatcttgga gccgcaggat      720
gtcgtccggt tcggagtctt cctctacacg ttgggctgcg tctgtgccgc ttgcctctac     780
tacctgtccc ctctgaaact ggagcacttg gctcttatct actttggagg cctgtctggc     840
tccttctct acacaggagg aattggattc aagtacgtgg ctctgggaga cctcatcatc     900
ctcatcactt ttggcccgct ggctgtgatg ttcgcctacg ccatccaggt ggggtccctg     960
gccatcttcc cactggtcta tgccatcccc ctcgccctca gcaccgaggc cattctccat    1020
tccaacaaca ccagggacat ggagtccgac cgggaggctg gtatcgtcac gctggccatc    1080
ctcatcggcc ccacgttctc ctacattctc tacaacacac tgctcttcct gccctacctg    1140
gtcttcagca tcctggccac acactgcacc atcagcctgg cactccccct gcttaccatt    1200
cccatggcct ctcccttga gacagttt cgaagccagg ccttcaacaa actgccccag      1260
aggactgcca agctcaacct cctgctggga cttttctatg tctttggcat cattctggca    1320
ccagcaggca gtctgcccaa aatttaaggg gacaagtagc tccccccacg acatgtctcc    1380
ctttcttaga atatattaaa gtcagagtct ctgaggaagg aatgtgattt ggcagtcagg    1440
gtactaagca tgggtgggaa ctcctgcctt ataaaaattg ttttgtgttc ttaaagataa    1500
aaaaaaaaaa aaaaaaa                                                   1517
```

<210> SEQ ID NO 4
<211> LENGTH: 338
<212> TYPE: PRT
<213> ORGANISM: Homo sapiens

<400> SEQUENCE: 4

```
Met Ala Ala Ser Gln Val Leu Gly Glu Lys Ile Asn Ile Leu Ser Gly
1               5                   10                  15

Glu Thr Val Lys Ala Gly Asp Arg Asp Pro Leu Gly Asn Asp Cys Pro
            20                  25                  30

Glu Gln Asp Arg Leu Pro Gln Arg Ser Trp Arg Gln Lys Cys Ala Ser
        35                  40                  45
```

```
Tyr Val Leu Ala Leu Arg Pro Trp Ser Phe Ser Ala Ser Leu Thr Pro
 50                  55                  60

Val Ala Leu Gly Ser Ala Leu Ala Tyr Arg Ser His Gly Val Leu Asp
 65                  70                  75                  80

Pro Arg Leu Leu Val Gly Cys Ala Val Ala Val Leu Ala Val His Gly
                 85                  90                  95

Ala Gly Asn Leu Val Asn Thr Tyr Tyr Asp Phe Ser Lys Gly Ile Gly
            100                 105                 110

His Lys Lys Ser Asp Asp Arg Thr Leu Val Asp Arg Ile Leu Glu Pro
        115                 120                 125

Gln Asp Val Val Arg Phe Gly Val Phe Leu Tyr Thr Leu Gly Cys Val
130                 135                 140

Cys Ala Ala Cys Leu Tyr Tyr Leu Ser Pro Leu Lys Leu Glu His Leu
145                 150                 155                 160

Ala Leu Ile Tyr Phe Gly Gly Leu Ser Gly Ser Phe Leu Tyr Thr Gly
                165                 170                 175

Gly Ile Gly Phe Lys Tyr Val Ala Leu Gly Asp Leu Ile Ile Leu Ile
            180                 185                 190

Thr Phe Gly Pro Leu Ala Val Met Phe Ala Tyr Ala Ile Gln Val Gly
        195                 200                 205

Ser Leu Ala Ile Phe Pro Leu Val Tyr Ala Ile Pro Leu Ala Leu Ser
210                 215                 220

Thr Glu Ala Ile Leu His Ser Asn Asn Thr Arg Asp Met Glu Ser Asp
225                 230                 235                 240

Arg Glu Ala Gly Ile Val Thr Leu Ala Ile Leu Ile Gly Pro Thr Phe
                245                 250                 255

Ser Tyr Ile Leu Tyr Asn Thr Leu Leu Phe Leu Pro Tyr Leu Val Phe
            260                 265                 270

Ser Ile Leu Ala Thr His Cys Thr Ile Ser Leu Ala Leu Pro Leu Leu
        275                 280                 285

Thr Ile Pro Met Ala Phe Ser Leu Glu Arg Gln Phe Arg Ser Gln Ala
290                 295                 300

Phe Asn Lys Leu Pro Gln Arg Thr Ala Lys Leu Asn Leu Leu Leu Gly
305                 310                 315                 320

Leu Phe Tyr Val Phe Gly Ile Ile Leu Ala Pro Ala Gly Ser Leu Pro
                325                 330                 335

Lys Ile

<210> SEQ ID NO 5
<211> LENGTH: 1517
<212> TYPE: DNA
<213> ORGANISM: Homo sapiens

<400> SEQUENCE: 5
ggccgcgaat tcggcacgag cggcgcacaa gatggcggct ctggcggcct aaagaaggcc    60
gcggccgcgg ctcagccgtg ggctctaacg cggggctggg ggccggagac agacttccag   120
gtgacgggta gtaggggcgg cgccgcttgg cctcgtgggg tgtaagaccc acttgctgtt   180
gcccccggac cttgccgcca caccagccct gtcctggggc ggaaccgaag gaaggtcggg   240
ccctgctgcc ccgccccgtc cttcctcctt cccgggcggt cactgtgcgt ggctcacttt   300
tagagtttac ttcaaccacg tggagcttcc atggcggcct ctcaggtcct gggggagaag   360
attaacatcc tgtcgggaga gactgtcaaa gctggggaca gggacccgct ggggaacgac   420
tgtcccgagc aagataggct ccccagcgc tcctggaggc agaagtgtgc ctcctacgtg   480
```

-continued

```
ttggccctga ggccctggag cttcagtgcc tcactcacac cggtggccct gggcagtgcc    540
cttgcctaca gatcccacgg tgtcctggat cccaggctct tggtgggttg tgccgtggct    600
gtcctggctg tgcacggggc cggtaatttg gtcaacactt actatgactt tccaagggc    660
attgaccaca aaaagagtga tgacgggaca cttgtggacc gaatcttgga gccgcaggat    720
gtcgtccggt tcggagtctt cctctacacg ttgggctgcg tctgtgccgc ttgcctctac    780
tacctgtccc ctctgaaact ggagcacttg gctcttatct actttggagg cctgtctggc    840
tcctttctct acacaggagg aattggattc aagtacgtgg ctctgggaga cctcatcatc    900
ctcatcactt ttggccccgct ggctgtgatg ttcgcctacg ccatccaggt ggggtccctg    960
gccatcttcc cactggtcta tgccatcccc ctcgccctca gcaccgaggc cattctccat   1020
tccaacaaca ccagggacat ggagtccgac cgggaggctg gtatcgtcac gctgccatc   1080
ctcatcggcc ccacgttctc ctacattctc tacaacacac tgctcttcct gccctacctg   1140
gtcttcagca tcctggccac acactgcacc atcagcctgg cactccccct gcttaccatt   1200
cccatggcct tctcccttga gagacagttt cgaagccagg ccttcaacaa actgccccag   1260
aggactgcca agctcaacct cctgctggga ctttttctatg tctttggcat cattctggca   1320
ccagcaggca gtctgcccaa aatttaaggg gacaagtagc tcccccacg acatgtctcc   1380
ctttcttaga atatattaaa gtcagagtct ctgaggaagg aatgtgattt ggcagtcagg   1440
gtactaagca tgggtgggaa ctcctgcctt ataaaaattg ttttgtgttc ttaaagataa   1500
aaaaaaaaaa aaaaaaa                                                  1517
```

<210> SEQ ID NO 6
<211> LENGTH: 338
<212> TYPE: PRT
<213> ORGANISM: Homo sapiens

<400> SEQUENCE: 6

```
Met Ala Ala Ser Gln Val Leu Gly Glu Lys Ile Asn Ile Leu Ser Gly
1               5                   10                  15

Glu Thr Val Lys Ala Gly Asp Arg Asp Pro Leu Gly Asn Asp Cys Pro
            20                  25                  30

Glu Gln Asp Arg Leu Pro Gln Arg Ser Trp Arg Gln Lys Cys Ala Ser
        35                  40                  45

Tyr Val Leu Ala Leu Arg Pro Trp Ser Phe Ser Ala Ser Leu Thr Pro
    50                  55                  60

Val Ala Leu Gly Ser Ala Leu Tyr Arg Ser His Gly Val Leu Asp
65                  70                  75                  80

Pro Arg Leu Leu Val Gly Cys Ala Val Ala Val Leu Ala Val His Gly
                85                  90                  95

Ala Gly Asn Leu Val Asn Thr Tyr Tyr Asp Phe Ser Lys Gly Ile Asp
            100                 105                 110

His Lys Lys Ser Asp Asp Gly Thr Leu Val Asp Arg Ile Leu Glu Pro
        115                 120                 125

Gln Asp Val Val Arg Phe Gly Val Phe Leu Tyr Thr Leu Gly Cys Val
    130                 135                 140

Cys Ala Ala Cys Leu Tyr Tyr Leu Ser Pro Leu Lys Leu Glu His Leu
145                 150                 155                 160

Ala Leu Ile Tyr Phe Gly Gly Leu Ser Gly Ser Phe Leu Tyr Thr Gly
                165                 170                 175

Gly Ile Gly Phe Lys Tyr Val Ala Leu Gly Asp Leu Ile Leu Ile
            180                 185                 190
```

```
Thr Phe Gly Pro Leu Ala Val Met Phe Ala Tyr Ala Ile Gln Val Gly
        195                 200                 205
Ser Leu Ala Ile Phe Pro Leu Val Tyr Ala Ile Pro Leu Ala Leu Ser
        210                 215                 220
Thr Glu Ala Ile Leu His Ser Asn Asn Thr Arg Asp Met Glu Ser Asp
225                 230                 235                 240
Arg Glu Ala Gly Ile Val Thr Leu Ala Ile Leu Ile Gly Pro Thr Phe
                245                 250                 255
Ser Tyr Ile Leu Tyr Asn Thr Leu Leu Phe Leu Pro Tyr Leu Val Phe
                260                 265                 270
Ser Ile Leu Ala Thr His Cys Thr Ile Ser Leu Ala Leu Pro Leu Leu
                275                 280                 285
Thr Ile Pro Met Ala Phe Ser Leu Glu Arg Gln Phe Arg Ser Gln Ala
        290                 295                 300
Phe Asn Lys Leu Pro Gln Arg Thr Ala Lys Leu Asn Leu Leu Leu Gly
305                 310                 315                 320
Leu Phe Tyr Val Phe Gly Ile Ile Leu Ala Pro Ala Gly Ser Leu Pro
                325                 330                 335
Lys Ile

<210> SEQ ID NO 7
<211> LENGTH: 1517
<212> TYPE: DNA
<213> ORGANISM: Homo sapiens

<400> SEQUENCE: 7
ggccgcgaat tcggcacgag cggcgcacaa gatggcggct ctggcggcct aaagaaggcc    60
gcggccgcgg ctcagccgtg ggctctaacg cggggctggg ggccggagac agacttccag   120
gtgacgggta gtaggggcgg cgccgcttgg cctcgtgggg tgtaagaccc acttgctgtt   180
gcccccggac cttgccgcca caccagccct gtcctgggc ggaaccgaag gaaggtcggg    240
ccctgctgcc ccgccccgtc cttcctcctt cccgggcggt cactgtgcgt ggctcacttt   300
tagagtttac ttcaaccacg tggagcttcc atggcggcct ctcaggtcct gggggagaag   360
attaacatcc tgtcgggaga gactgtcaaa gctggggaca gggacccgct ggggaacgac   420
tgtcccgagc aagataggct ccccccagcgc tcctggaggc agaagtgtgc ctcctacgtg   480
ttggccctga ggccctggag cttcagtgcc tcactcacac cggtggccct gggcagtgcc   540
cttgcctaca gatcccacgg tgtcctggat cccaggctct tggtgggttg tgccgtggct   600
gtcctggctg tgcacggggc cggtaatttg gtcaacactt actatgactt ttccaagggc   660
attgaccaca aaaagagtga tgacaggaca cttgtggacc gaatcttgga gccgcaggat   720
gtcgtccggt tcggagtctt cctctacacg ttgggctgcg tctgtgccgc ttgcctctac   780
tacctgtccc ctctgaaact ggagcacttg gctcttatct actttggagg cctgtctggc   840
tcctttctct acataggagg aattggattg aagtacgtgg ctctgggaga cctcatcatc   900
ctcatcactt ttggcccgct ggctgtgatg ttcgcctacg ccatccaggt ggggtccctg   960
gccatcttcc cactggtcta tgccatcccc ctcgccctca gcaccgaggc cattctccat  1020
tccaacaaca ccagggacat ggagtccgac cgggaggctg gtatcgtcac gctggccatc  1080
ctcatcggcc ccacgttctc ctacattctc tacaacacac tgctcttcct gccctacctg  1140
gtcttcagca tcctggccac acactgcacc atcagcctgg cactccccct gcttaccatt  1200
cccatggcct ctcccttga gagacagttt cgaagccagg ccttcaacaa actgccccag  1260
aggactgcca agctcaacct cctgctggga cttttctatg tctttggcat cattctggca  1320
```

```
ccagcaggca gtctgcccaa aatttaaggg gacaagtagc tcccccacg acatgtctcc    1380 ctttcttaga atatattaaa gtcagagtct ctgaggaagg aatgtgattt ggcagtcagg    1440
gtactaagca tgggtgggaa ctcctgcctt ataaaaattg ttttgtgttc ttaaagataa    1500
aaaaaaaaaa aaaaaaa                                                    1517
```

<210> SEQ ID NO 8
<211> LENGTH: 338
<212> TYPE: PRT
<213> ORGANISM: Homo sapiens

<400> SEQUENCE: 8

```
Met Ala Ala Ser Gln Val Leu Gly Glu Lys Ile Asn Ile Leu Ser Gly
1               5                   10                  15

Glu Thr Val Lys Ala Gly Asp Arg Asp Pro Leu Gly Asn Asp Cys Pro
                20                  25                  30

Glu Gln Asp Arg Leu Pro Gln Arg Ser Trp Arg Gln Lys Cys Ala Ser
            35                  40                  45

Tyr Val Leu Ala Leu Arg Pro Trp Ser Phe Ser Ala Ser Leu Thr Pro
        50                  55                  60

Val Ala Leu Gly Ser Ala Leu Ala Tyr Arg Ser His Gly Val Leu Asp
65                  70                  75                  80

Pro Arg Leu Leu Val Gly Cys Ala Val Ala Val Leu Ala Val His Gly
                85                  90                  95

Ala Gly Asn Leu Val Asn Thr Tyr Tyr Asp Phe Ser Lys Gly Ile Asp
            100                 105                 110

His Lys Lys Ser Asp Asp Arg Thr Leu Val Asp Arg Ile Leu Glu Pro
        115                 120                 125

Gln Asp Val Val Arg Phe Gly Val Phe Leu Tyr Thr Leu Gly Cys Val
    130                 135                 140

Cys Ala Ala Cys Leu Tyr Tyr Leu Ser Pro Leu Lys Leu Glu His Leu
145                 150                 155                 160

Ala Leu Ile Tyr Phe Gly Gly Leu Ser Gly Ser Phe Leu Tyr Ile Gly
                165                 170                 175

Gly Ile Gly Phe Lys Tyr Val Ala Leu Gly Asp Leu Ile Ile Leu Ile
            180                 185                 190

Thr Phe Gly Pro Leu Ala Val Met Phe Ala Tyr Ala Ile Gln Val Gly
        195                 200                 205

Ser Leu Ala Ile Phe Pro Leu Val Tyr Ala Ile Pro Leu Ala Leu Ser
    210                 215                 220

Thr Glu Ala Ile Leu His Ser Asn Asn Thr Arg Asp Met Glu Ser Asp
225                 230                 235                 240

Arg Glu Ala Gly Ile Val Thr Leu Ala Ile Leu Ile Gly Pro Thr Phe
                245                 250                 255

Ser Tyr Ile Leu Tyr Asn Thr Leu Phe Leu Pro Tyr Leu Val Phe
            260                 265                 270

Ser Ile Leu Ala Thr His Cys Thr Ile Ser Leu Ala Leu Pro Leu Leu
        275                 280                 285

Thr Ile Pro Met Ala Phe Ser Leu Glu Arg Gln Phe Arg Ser Gln Ala
    290                 295                 300

Phe Asn Lys Leu Pro Gln Arg Thr Ala Lys Leu Asn Leu Leu Leu Gly
305                 310                 315                 320

Leu Phe Tyr Val Phe Gly Ile Ile Leu Ala Pro Ala Gly Ser Leu Pro
                325                 330                 335
```

Lys Ile

<210> SEQ ID NO 9
<211> LENGTH: 1517
<212> TYPE: DNA
<213> ORGANISM: Homo sapiens

<400> SEQUENCE: 9

```
ggccgcgaat cggcacgag cggcgcacaa gatggcggct ctggcggcct aaagaaggcc      60
gcggccgcgg ctcagccgtg ggctctaacg cggggctggg ggccggagac agacttccag    120
gtgacgggta gtaggggcgg cgccgcttgg cctcgtgggg tgtaagaccc acttgctgtt    180
gcccccggac cttgccgcca ccagccct gtcctggggc ggaaccgaag gaaggtcggg       240
ccctgctgcc ccgccccgtc cttcctcctt cccggggcggt cactgtgcgt ggctcacttt    300
tagagtttac ttcaaccacg tggagcttcc atggcggcct ctcaggtcct ggggagaag     360
attaacatcc tgtcgggaga gactgtcaaa gctggggaca gggacccgct ggggaacgac    420
tgtcccgagc aagataggct ccccagcgc tcctggaggc agaagtgtgc ctcctacgtg     480
ttggcccctga ggcctggag cttcagtgcc tcactcacac cggtggccct gggcagtgcc    540
cttgcctaca gatcccacgg tgtcctggat cccaggctct tggtgggttg tgccgtggct    600
gtcctggctg tgcacgggc cggtaatttg gtcaacactt actatgactt ttccaagggc    660
attgaccaca aaagagtga tgacaggaca cttgtggacc gaatcttgga gccgcaggat    720
gtcgtccggt tcggagtctt cctctacacg ttgggctgcg tctgtgccgc ttgcctctac    780
tacctgtccc ctctgaaact ggagcacttg gctcttatct actttggagg cctgtctggc    840
tcctttctct acacaggagg aattggattc aagtacgtgg ctctgggaga cctcatcatc    900
ctcatcactt ttggcccgct ggctgtgatg ttcgcctacg ccatccaggt ggggtccctg    960
gccatcttcc cactggtcta tgccatcccc ctcgccctca gcaccgaggc cattctccat   1020
tccagcaaca ccagggacat ggagtccgac cgggaggctg gtatcgtcac gctggccatc   1080
ctcatcggcc ccacgttctc ctacattctc tacaacacac tgctcttcct gccctacctg   1140
gtcttcagca tcctggccac acactgcacc atcagcctgg cactccccct gcttaccatt   1200
cccatggcct tctcccttga gagacagttt cgaagccagg ccttcaacaa actgccccag   1260
aggactgcca agctcaacct cctgctggga cttttctatg tctttggcat cattctggca   1320
ccagcaggca gtctgcccaa aatttaaggg gacaagtagc tccccccacg acatgtctcc   1380
ctttcttaga atatattaaa gtcagagtct ctgaggaaga aatgtgattt ggcagtcagg   1440
gtactaagca tgggtgggaa ctcctgcctt ataaaaattg ttttgtgttc ttaaagataa   1500
aaaaaaaaaa aaaaaaa                                                   1517
```

<210> SEQ ID NO 10
<211> LENGTH: 338
<212> TYPE: PRT
<213> ORGANISM: Homo sapiens

<400> SEQUENCE: 10

Met Ala Ala Ser Gln Val Leu Gly Glu Lys Ile Asn Ile Leu Ser Gly
1               5                   10                  15

Glu Thr Val Lys Ala Gly Asp Arg Asp Pro Leu Gly Asn Asp Cys Pro
            20                  25                  30

Glu Gln Asp Arg Leu Pro Gln Arg Ser Trp Arg Gln Lys Cys Ala Ser
        35                  40                  45

Tyr Val Leu Ala Leu Arg Pro Trp Ser Phe Ser Ala Ser Leu Thr Pro

| | | 50 | | | 55 | | | 60 | | | |

Val Ala Leu Gly Ser Ala Leu Ala Tyr Arg Ser His Gly Val Leu Asp
65                  70                  75                  80

Pro Arg Leu Leu Val Gly Cys Ala Val Ala Val Leu Ala Val His Gly
                    85                  90                  95

Ala Gly Asn Leu Val Asn Thr Tyr Tyr Asp Phe Ser Lys Gly Ile Asp
            100                 105                 110

His Lys Lys Ser Asp Asp Arg Thr Leu Val Asp Arg Ile Leu Glu Pro
        115                 120                 125

Gln Asp Val Val Arg Phe Gly Val Phe Leu Tyr Thr Leu Gly Cys Val
    130                 135                 140

Cys Ala Ala Cys Leu Tyr Tyr Leu Ser Pro Leu Lys Leu Glu His Leu
145                 150                 155                 160

Ala Leu Ile Tyr Phe Gly Gly Leu Ser Gly Ser Phe Leu Tyr Thr Gly
                165                 170                 175

Gly Ile Gly Phe Lys Tyr Val Ala Leu Gly Asp Leu Ile Ile Leu Ile
            180                 185                 190

Thr Phe Gly Pro Leu Ala Val Met Phe Ala Tyr Ala Ile Gln Val Gly
        195                 200                 205

Ser Leu Ala Ile Phe Pro Leu Val Tyr Ala Ile Pro Leu Ala Leu Ser
    210                 215                 220

Thr Glu Ala Ile Leu His Ser Ser Asn Thr Arg Asp Met Glu Ser Asp
225                 230                 235                 240

Arg Glu Ala Gly Ile Val Thr Leu Ala Ile Leu Ile Gly Pro Thr Phe
                245                 250                 255

Ser Tyr Ile Leu Tyr Asn Thr Leu Leu Phe Leu Pro Tyr Leu Val Phe
            260                 265                 270

Ser Ile Leu Ala Thr His Cys Thr Ile Ser Leu Ala Leu Pro Leu Leu
        275                 280                 285

Thr Ile Pro Met Ala Phe Ser Leu Glu Arg Gln Phe Arg Ser Gln Ala
    290                 295                 300

Phe Asn Lys Leu Pro Gln Arg Thr Ala Lys Leu Asn Leu Leu Leu Gly
305                 310                 315                 320

Leu Phe Tyr Val Phe Gly Ile Ile Leu Ala Pro Ala Gly Ser Leu Pro
                325                 330                 335

Lys Ile

<210> SEQ ID NO 11
<211> LENGTH: 1517
<212> TYPE: DNA
<213> ORGANISM: Homo sapiens

<400> SEQUENCE: 11

```
ggccgcgaat tcggcacgag cggcgcacaa gatggcggct ctggcggcct aaagaaggcc     60
gcggccgcgg ctcagccgtg ggctctaacg cggggctggg ggccggagac agacttccag    120
gtgacgggta gtaggggcgg cgccgcttgg cctcgtgggg tgtaagaccc acttgctgtt    180
gcccccggac cttgccgcca caccagccct gtcctggggc ggaaccgaag gaaggtcggg    240
ccctgctgcc ccgccccgtc cttcctcctt cccggcggt cactgtgcgt ggctcacttt     300
tagagtttac ttcaaccacg tggagcttcc atggcggcct caggtcct ggggagaag       360
attaacatcc tgtcgggaga gactgtcaaa gctgggaca gggacccgct ggggaacgac     420
tgtcccgagc aagataggct ccccagcgc tcctggaggc agaagtgtgc ctcctacgtg     480
ttggccctga ggcctggag cttcagtgcc tcactcacac cggtggccct gggcagtgcc    540
```

```
cttgcctaca gattccacgg tgtcctggat cccaggctct tggtggggttg tgccgtggct   600
gtcctggctg tgcacggggc cggtaatttg gtcaacactt actatgactt ttccaagggc   660
attgaccaca aaaagagtga tgacaggaca cttgtggacc gaatcttgga gccgcaggat   720
gtcgtccggt tcggagtctt cctctacacg ttgggctgcg tctgtgccgc ttgcctctac   780
tacctgtccc ctctgaaact ggagcacttg gctcttatct actttggagg cctgtctggc   840
tcctttctct acacaggagg aattggattc aagtacgtgg ctctgggaga cctcatcatc   900
ctcatcactt ttggcccgct ggctgtgatg ttcgcctacg ccatccaggt ggggtccctg   960
gccatcttcc cactggtcta tgccatcccc ctcgccctca gcaccgaggc cattctccat  1020
tccaacaaca ccagggacat ggagtccgac cgggaggctg gtatcgtcac gctggccatc  1080
ctcatcggcc ccacgttctc ctacattctc tacaacacac tgctcttcct gccctacctg  1140
gtcttcagca tcctggccac acactgcacc atcagcctgg cactccccct gcttaccatt  1200
cccatggcct tctcccttga gacagtttt cgaagccagg ccttcaacaa actgccccag  1260
aggactgcca agctcaacct cctgctggga cttttctatg tctttggcat cattctggca  1320
ccagcaggca gtctgcccaa aatttaaggg gacaagtagc tccccccacg acatgtctcc  1380
ctttcttaga atatattaaa gtcagagtct ctgaggaagg aatgtgattt ggcagtcagg  1440
gtactaagca tgggtgggaa ctcctgcctt ataaaaattg ttttgtgttc ttaaagataa  1500
aaaaaaaaaa aaaaaaa                                                 1517

<210> SEQ ID NO 12
<211> LENGTH: 338
<212> TYPE: PRT
<213> ORGANISM: Homo sapiens

<400> SEQUENCE: 12

Met Ala Ala Ser Gln Val Leu Gly Glu Lys Ile Asn Ile Leu Ser Gly
1               5                   10                  15

Glu Thr Val Lys Ala Gly Asp Arg Asp Pro Leu Gly Asn Asp Cys Pro
            20                  25                  30

Glu Gln Asp Arg Leu Pro Gln Arg Ser Trp Arg Gln Lys Cys Ala Ser
        35                  40                  45

Tyr Val Leu Ala Leu Arg Pro Trp Ser Phe Ser Ala Ser Leu Thr Pro
    50                  55                  60

Val Ala Leu Gly Ser Ala Leu Ala Tyr Arg Phe His Gly Val Leu Asp
65                  70                  75                  80

Pro Arg Leu Leu Val Gly Cys Ala Val Ala Val Leu Ala Val His Gly
                85                  90                  95

Ala Gly Asn Leu Val Asn Thr Tyr Tyr Asp Phe Ser Lys Gly Ile Asp
            100                 105                 110

His Lys Lys Ser Asp Asp Arg Thr Leu Val Asp Arg Ile Leu Glu Pro
        115                 120                 125

Gln Asp Val Val Arg Phe Gly Val Phe Leu Tyr Thr Leu Gly Cys Val
    130                 135                 140

Cys Ala Ala Cys Leu Tyr Tyr Leu Ser Pro Leu Lys Leu Glu His Leu
145                 150                 155                 160

Ala Leu Ile Tyr Phe Gly Gly Leu Ser Gly Ser Phe Leu Tyr Thr Gly
                165                 170                 175

Gly Ile Gly Phe Lys Tyr Val Ala Leu Gly Asp Leu Ile Ile Leu Ile
            180                 185                 190

Thr Phe Gly Pro Leu Ala Val Met Phe Ala Tyr Ala Ile Gln Val Gly
```

```
                195              200              205
Ser Leu Ala Ile Phe Pro Leu Val Tyr Ala Ile Pro Leu Ala Leu Ser
    210                 215                 220

Thr Glu Ala Ile Leu His Ser Asn Asn Thr Arg Asp Met Glu Ser Asp
225                 230                 235                 240

Arg Glu Ala Gly Ile Val Thr Leu Ala Ile Leu Ile Gly Pro Thr Phe
                245                 250                 255

Ser Tyr Ile Leu Tyr Asn Thr Leu Leu Phe Leu Pro Tyr Leu Val Phe
            260                 265                 270

Ser Ile Leu Ala Thr His Cys Thr Ile Ser Leu Ala Leu Pro Leu Leu
        275                 280                 285

Thr Ile Pro Met Ala Phe Ser Leu Glu Arg Gln Phe Arg Ser Gln Ala
    290                 295                 300

Phe Asn Lys Leu Pro Gln Arg Thr Ala Lys Leu Asn Leu Leu Leu Gly
305                 310                 315                 320

Leu Phe Tyr Val Phe Gly Ile Ile Leu Ala Pro Ala Gly Ser Leu Pro
                325                 330                 335

Lys Ile

<210> SEQ ID NO 13
<211> LENGTH: 69
<212> TYPE: DNA
<213> ORGANISM: Homo sapiens

<400> SEQUENCE: 13
gtgcatggcg cgggcaacct ggtgaacacc tattatgatt ttagcaaagg cattgatcat    60
aaaaaaagc                                                            69

<210> SEQ ID NO 14
<211> LENGTH: 23
<212> TYPE: PRT
<213> ORGANISM: Homo sapiens

<400> SEQUENCE: 14

Val His Gly Ala Gly Asn Leu Val Asn Thr Tyr Tyr Asp Phe Ser Lys
1               5                   10                  15

Gly Ile Asp His Lys Lys Ser
            20

<210> SEQ ID NO 15
<211> LENGTH: 51
<212> TYPE: DNA
<213> ORGANISM: Homo sapiens

<400> SEQUENCE: 15
attctgcata gcagcaacac ccgcgatatg gaaagcgatc gcgaagcggg c              51

<210> SEQ ID NO 16
<211> LENGTH: 17
<212> TYPE: PRT
<213> ORGANISM: Homo sapiens

<400> SEQUENCE: 16

Ile Leu His Ser Ser Asn Thr Arg Asp Met Glu Ser Asp Arg Glu Ala
1               5                   10                  15

Gly

<210> SEQ ID NO 17
<211> LENGTH: 1518
```

<212> TYPE: DNA
<213> ORGANISM: Homo sapiens

<400> SEQUENCE: 17

```
ggccgcgaat tcggcacgag cggcgcacaa gatggcggct ctggcggcct aaagaaggcg      60
gccgcggctc agccgtgggc tctaacgcgg ggctggggc cggagacaga cttcgcccag     120
gtgacgggta gtaggggcgg cgccgcttgg cctcgtgggg tgtaagaccc acttgctgtt    180
gcccccggac cttgccgcca caccagccct gtcctgggc ggaaccgaag gaaggtcggg     240
ccctgctgcc ccgccccgtc cttcctcctt cccgggcggt cactgtgcgt ggctcacttt    300
tagagtttac ttcaaccacg tggagcttcc atggcggcct ctcaggtcct ggggagaag     360
attaacatcc tgtcgggaga gactgtcaaa gctggggaca gggacccgct ggggaacgac    420
tgtcccgagc aagataggct cccccagcgc tcctggaggc agaagtgtgc ctcctacgtg    480
ttggccctga ggccctggag cttcagtgcc tcactcacac cggtggccct gggcagtgcc    540
cttgcctaca gatcccacgg tgtcctggat cccaggctct tggtgggttg tgccgtggct    600
gtcctggctg tgcacggggc cggtaatttg gtcaacactt actatgactt ttccaagggc    660
attgaccaca aaaagagtga tgacaggaca cttgtggacc gaatcttgga gccgcaggat    720
gtcgtccggt tcggagtctt cctctacacg ttgggctgcg tctgtgccgc ttgcctctac    780
tacctgtccc ctctgaaact ggagcacttg gctcttatct actttggagg cctgtctggc    840
tcctttctct acacaggagg aattggattc aagtacgtgg ctctgggaga cctcatcatc    900
ctcatcactt ttggcccgct ggctgtgatg ttcgcctacg ccatccaggt ggggtccctg    960
gccatcttcc cactggtcta tgccatcccc ctcgccctca gcaccgaggc cattctccat   1020
tccaacaaca ccagggacat ggagtccgac cgggaggctg gtatcgtcac gctggccatc   1080
ctcatcggcc ccacgttctc ctacattctc tacaacacac tgctcttcct gccctacctg   1140
gtcttcagca tcctggccac acactgcacc atcagcctgg cactccccct gcttaccatt   1200
cccatggcct tctcccttga gagacagttt cgaagccagg ccttcaacaa actgccccag   1260
aggactgcca agctcaacct cctgctggga ctttttctatg tctttggcat cattctggca   1320
ccagcaggca gtctgcccaa aatttaaggg gacaagtagc tcccccacg acatgtctcc    1380
ctttcttaga atatattaaa gtcagagtct ctgaggaagg aatgtgattt ggcagtcagg   1440
gtactaagca tgggtgggaa ctcctgcctt ataaaaattg tttttgtgtt cttaaagata   1500
aaaaaaaaaa aaaaaaaa                                                  1518
```

<210> SEQ ID NO 18
<211> LENGTH: 338
<212> TYPE: PRT
<213> ORGANISM: Homo sapiens

<400> SEQUENCE: 18

```
Met Ala Ala Ser Gln Val Leu Gly Glu Lys Ile Asn Ile Leu Ser Gly
1               5                   10                  15
Glu Thr Val Lys Ala Gly Asp Arg Asp Pro Leu Gly Asn Asp Cys Pro
            20                  25                  30
Glu Gln Asp Arg Leu Pro Gln Arg Ser Trp Arg Gln Lys Cys Ala Ser
        35                  40                  45
Tyr Val Leu Ala Leu Arg Pro Trp Ser Phe Ser Ala Ser Leu Thr Pro
    50                  55                  60
Val Ala Leu Gly Ser Ala Leu Ala Tyr Arg Ser His Gly Val Leu Asp
65                  70                  75                  80
```

```
Pro Arg Leu Leu Val Gly Cys Ala Val Ala Val Leu Ala Val His Gly
            85                  90                  95

Ala Gly Asn Leu Val Asn Thr Tyr Tyr Asp Phe Ser Lys Gly Ile Asp
            100                 105                 110

His Lys Lys Ser Asp Asp Arg Thr Leu Val Asp Arg Ile Leu Glu Pro
            115                 120                 125

Gln Asp Val Val Arg Phe Gly Val Phe Leu Tyr Thr Leu Gly Cys Val
            130                 135                 140

Cys Ala Ala Cys Leu Tyr Tyr Leu Ser Pro Leu Lys Leu Glu His Leu
145                 150                 155                 160

Ala Leu Ile Tyr Phe Gly Gly Leu Ser Gly Ser Phe Leu Tyr Thr Gly
            165                 170                 175

Gly Ile Gly Phe Lys Tyr Val Ala Leu Gly Asp Leu Ile Ile Leu Ile
            180                 185                 190

Thr Phe Gly Pro Leu Ala Val Met Phe Ala Tyr Ala Ile Gln Val Gly
            195                 200                 205

Ser Leu Ala Ile Phe Pro Leu Val Tyr Ala Ile Pro Leu Ala Leu Ser
            210                 215                 220

Thr Glu Ala Ile Leu His Ser Asn Asn Thr Arg Asp Met Glu Ser Asp
225                 230                 235                 240

Arg Glu Ala Gly Ile Val Thr Leu Ala Ile Leu Ile Gly Pro Thr Phe
            245                 250                 255

Ser Tyr Ile Leu Tyr Asn Thr Leu Leu Phe Leu Pro Tyr Leu Val Phe
            260                 265                 270

Ser Ile Leu Ala Thr His Cys Thr Ile Ser Leu Ala Leu Pro Leu Leu
            275                 280                 285

Thr Ile Pro Met Ala Phe Ser Leu Glu Arg Gln Phe Arg Ser Gln Ala
            290                 295                 300

Phe Asn Lys Leu Pro Gln Arg Thr Ala Lys Leu Asn Leu Leu Leu Gly
305                 310                 315                 320

Leu Phe Tyr Val Phe Gly Ile Ile Leu Ala Pro Ala Gly Ser Leu Pro
            325                 330                 335

Lys Ile

<210> SEQ ID NO 19
<211> LENGTH: 1014
<212> TYPE: DNA
<213> ORGANISM: Homo sapiens

<400> SEQUENCE: 19
atggcggcct ctcaggtcct gggggagaag attaacatcc tgtcgggaga gactgtcaaa      60
gctggggaca gggacccgct ggggaacgac tgtcccgagc aagataggct cccccagcgc     120
tcctggaggc agaagtgtgc ctcctacgtg ttggccctga ggccctggag cttcagtgcc     180
tcactcacac cggtggccct gggcagtgcc cttgcctaca gatcccacgg tgtcctggat     240
cccaggctct tggtgggttg tgccgtggct gtcctggctg tgcacggggc cggtaatttg     300
gtcagcactt actatgactt ttccaagggc attgaccaca aaaagagtga tgacaggaca     360
cttgtggacc gaatcttgga gccgcaggat gtcgtccggt tcggagtctt cctctacacg     420
ttgggctgcg tctgtgccgc ttgcctctac tacctgtccc ctctgaaact ggagcacttg     480
gctcttatct actttggagg cctgtctggc tcctttctct acacaggagg aattggattc     540
aagtacgtgg ctctgggaga cctcatcatc ctcatcactt ttggcccgct ggctgtgatg     600
ttcgcctacg ccatccaggt ggggtccctg gccatcttcc cactggtcta tgccatcccc     660
```

| | |
|---|---|
| ctcgccctca gcaccgaggc cattctccat tccaacaaca ccagggacat ggagtccgac | 720 |
| cgggaggctg gtatcgtcac gctggccatc ctcatcggcc ccacgttctc ctacattctc | 780 |
| tacaacacac tgctcttcct gccctacctg gtcttcagca tcctggccac acactgcacc | 840 |
| atcagcctgg cactccccct gcttaccatt cccatggcct tctcccttga gagacagttt | 900 |
| cgaagccagg ccttcaacaa actgccccag aggactgcca agctcaacct cctgctggga | 960 |
| cttttctatg tctttggcat cattctggca ccagcaggca gtctgcccaa aatt | 1014 |

<210> SEQ ID NO 20
<211> LENGTH: 1014
<212> TYPE: DNA
<213> ORGANISM: Homo sapiens

<400> SEQUENCE: 20

| | |
|---|---|
| atggcggcct ctcaggtcct gggggagaag attaacatcc tgtcgggaga gactgtcaaa | 60 |
| gctggggaca gggacccgct ggggaacgac tgtcccgagc aagataggct cccccagcgc | 120 |
| tcctggaggc agaagtgtgc ctcctacgtg ttggccctga ggcctggag cttcagtgcc | 180 |
| tcactcacac cggtggccct gggcagtgcc cttgcctaca gatcccacgg tgtcctggat | 240 |
| cccaggctct tggtgggttg tgccgtggct gtcctggctg tgcacggggc cggtaatttg | 300 |
| gtcaacactt actatgactt ttccaagggc attggccaca aaaagagtga tgacaggaca | 360 |
| cttgtggacc gaatcttgga gccgcaggat gtcgtccggt tcggagtctt cctctacacg | 420 |
| ttgggctgcg tctgtgccgc ttgcctctac tacctgtccc ctctgaaact ggagcacttg | 480 |
| gctcttatct actttggagg cctgtctggc tcctttctct acacaggagg aattggattc | 540 |
| aagtacgtgg ctctgggaga cctcatcatc ctcatcactt ttggcccgct ggctgtgatg | 600 |
| ttcgcctacg ccatccaggt ggggtccctg gccatcttcc cactggtcta tgccatcccc | 660 |
| ctcgccctca gcaccgaggc cattctccat tccaacaaca ccagggacat ggagtccgac | 720 |
| cgggaggctg gtatcgtcac gctggccatc ctcatcggcc ccacgttctc ctacattctc | 780 |
| tacaacacac tgctcttcct gccctacctg gtcttcagca tcctggccac acactgcacc | 840 |
| atcagcctgg cactccccct gcttaccatt cccatggcct tctcccttga gagacagttt | 900 |
| cgaagccagg ccttcaacaa actgccccag aggactgcca agctcaacct cctgctggga | 960 |
| cttttctatg tctttggcat cattctggca ccagcaggca gtctgcccaa aatt | 1014 |

<210> SEQ ID NO 21
<211> LENGTH: 1014
<212> TYPE: DNA
<213> ORGANISM: Homo sapiens

<400> SEQUENCE: 21

| | |
|---|---|
| atggcggcct ctcaggtcct gggggagaag attaacatcc tgtcgggaga gactgtcaaa | 60 |
| gctggggaca gggacccgct ggggaacgac tgtcccgagc aagataggct cccccagcgc | 120 |
| tcctggaggc agaagtgtgc ctcctacgtg ttggccctga ggcctggag cttcagtgcc | 180 |
| tcactcacac cggtggccct gggcagtgcc cttgcctaca gatcccacgg tgtcctggat | 240 |
| cccaggctct tggtgggttg tgccgtggct gtcctggctg tgcacggggc cggtaatttg | 300 |
| gtcaacactt actatgactt ttccaagggc attgaccaca aaaagagtga tgacgggaca | 360 |
| cttgtggacc gaatcttgga gccgcaggat gtcgtccggt tcggagtctt cctctacacg | 420 |
| ttgggctgcg tctgtgccgc ttgcctctac tacctgtccc ctctgaaact ggagcacttg | 480 |
| gctcttatct actttggagg cctgtctggc tcctttctct acacaggagg aattggattc | 540 |

```
aagtacgtgg ctctgggaga cctcatcatc ctcatcactt ttggcccgct ggctgtgatg    600
ttcgcctacg ccatccaggt ggggtccctg gccatcttcc cactggtcta tgccatcccc    660
ctcgccctca gcaccgaggc cattctccat tccaacaaca ccagggacat ggagtccgac    720
cgggaggctg gtatcgtcac gctggccatc ctcatcggcc ccacgttctc ctacattctc    780
tacaacacac tgctcttcct gccctacctg gtcttcagca tcctggccac acactgcacc    840
atcagcctgg cactccccct gcttaccatt cccatggcct ctcccttga gagacagttt    900 cgaagccagg ccttcaacaa actgccccag aggactgcca agctcaacct cctgctggga    960
cttttctatg tctttggcat cattctggca ccagcaggca gtctgcccaa aatt         1014

<210> SEQ ID NO 22
<211> LENGTH: 1014
<212> TYPE: DNA
<213> ORGANISM: Homo sapiens

<400> SEQUENCE: 22
atggcggcct ctcaggtcct gggggagaag attaacatcc tgtcgggaga gactgtcaaa    60
gctggggaca gggacccgct ggggaacgac tgtcccgagc aagataggct cccccagcgc    120
tcctggaggc agaagtgtgc ctcctacgtg ttggccctga ggccctggag cttcagtgcc    180
tcactcacac cggtggccct gggcagtgcc cttgcctaca gatcccacgg tgtcctggat    240
cccaggctct tggtgggttg tgccgtggct gtcctggctg tgcacggggc cggtaatttg    300
gtcaacactt actatgactt ttccaagggc attgaccaca aaaagagtga tgacaggaca    360
cttgtggacc gaatcttgga gccgcaggat gtcgtccggt tcggagtctt cctctacacg    420
ttgggctgcg tctgtgccgc ttgcctctac tacctgtccc ctctgaaact ggagcacttg    480
gctcttatct actttggagg cctgtctggc tcctttctct acataggagg aattggattg    540
aagtacgtgg ctctgggaga cctcatcatc ctcatcactt ttggcccgct ggctgtgatg    600
ttcgcctacg ccatccaggt ggggtccctg gccatcttcc cactggtcta tgccatcccc    660
ctcgccctca gcaccgaggc cattctccat tccaacaaca ccagggacat ggagtccgac    720
cgggaggctg gtatcgtcac gctggccatc ctcatcggcc ccacgttctc ctacattctc    780
tacaacacac tgctcttcct gccctacctg gtcttcagca tcctggccac acactgcacc    840
atcagcctgg cactccccct gcttaccatt cccatggcct ctcccttga gagacagttt    900 cgaagccagg ccttcaacaa actgccccag aggactgcca agctcaacct cctgctggga    960
cttttctatg tctttggcat cattctggca ccagcaggca gtctgcccaa aatt         1014

<210> SEQ ID NO 23
<211> LENGTH: 1014
<212> TYPE: DNA
<213> ORGANISM: Homo sapiens

<400> SEQUENCE: 23
atggcggcct ctcaggtcct gggggagaag attaacatcc tgtcgggaga gactgtcaaa    60
gctggggaca gggacccgct ggggaacgac tgtcccgagc aagataggct cccccagcgc    120
tcctggaggc agaagtgtgc ctcctacgtg ttggccctga ggccctggag cttcagtgcc    180
tcactcacac cggtggccct gggcagtgcc cttgcctaca gatcccacgg tgtcctggat    240
cccaggctct tggtgggttg tgccgtggct gtcctggctg tgcacggggc cggtaatttg    300
gtcaacactt actatgactt ttccaagggc attgaccaca aaaagagtga tgacaggaca    360
cttgtggacc gaatcttgga gccgcaggat gtcgtccggt tcggagtctt cctctacacg    420
```

```
ttgggctgcg tctgtgccgc ttgcctctac tacctgtccc ctctgaaact ggagcacttg    480
gctcttatct actttggagg cctgtctggc tcctttctct acacaggagg aattggattc    540
aagtacgtgg ctctgggaga cctcatcatc ctcatcactt ttggcccgct ggctgtgatg    600
ttcgcctacg ccatccaggt gggggtccctg gccatcttcc cactggtcta tgccatcccc    660
ctcgccctca gcaccgaggc cattctccat ccagcaaca ccagggacat ggagtccgac    720
cgggaggctg gtatcgtcac gctggccatc ctcatcggcc ccacgttctc ctacattctc    780
tacaacacac tgctcttcct gccctacctg gtcttcagca tcctggccac acactgcacc    840
atcagcctgg cactcccccct gcttaccatt cccatggcct ctcccttga gacagtttt    900
cgaagccagg ccttcaacaa actgccccag aggactgcca agctcaacct cctgctggga    960
cttttctatg tctttggcat cattctggca ccagcaggca gtctgcccaa aatt         1014

<210> SEQ ID NO 24
<211> LENGTH: 338
<212> TYPE: PRT
<213> ORGANISM: Pan troglodytes

<400> SEQUENCE: 24

Met Ala Ala Ser Gln Val Leu Gly Gln Lys Ile Asn Ile Leu Ser Gly
1               5                   10                  15

Glu Thr Val Lys Ala Gly Asp Arg Asp Pro Leu Gly Asn Asp Cys Pro
            20                  25                  30

Glu Gln Asp Arg Leu Pro Gln Arg Ser Trp Arg Gln Lys Cys Ala Ser
        35                  40                  45

Tyr Val Leu Ala Leu Arg Pro Trp Ser Phe Ser Ala Ser Leu Thr Pro
    50                  55                  60

Val Ala Leu Gly Ser Ala Leu Ala Tyr Arg Ser His Gly Val Leu Asp
65                  70                  75                  80

Pro Arg Leu Leu Val Gly Cys Ala Val Ala Val Leu Ala Val His Gly
                85                  90                  95

Ala Gly Asn Leu Val Asn Thr Tyr Tyr Asp Phe Ser Lys Gly Ile Asp
            100                 105                 110

His Lys Lys Ser Asp Asp Arg Thr Leu Val Asp Arg Ile Leu Glu Pro
        115                 120                 125

Gln Asp Val Val Arg Phe Gly Val Phe Leu Tyr Thr Leu Gly Cys Val
    130                 135                 140

Cys Ala Ala Cys Leu Tyr Tyr Leu Ser Pro Leu Lys Leu Glu His Leu
145                 150                 155                 160

Ala Leu Ile Tyr Phe Gly Gly Leu Ser Gly Ser Phe Leu Tyr Thr Gly
                165                 170                 175

Gly Ile Gly Phe Lys Tyr Val Ala Leu Gly Asp Leu Ile Leu Ile
            180                 185                 190

Thr Phe Gly Pro Leu Ala Val Met Phe Ala Tyr Ala Ile Gln Val Gly
        195                 200                 205

Ser Leu Ala Ile Phe Pro Leu Val Tyr Ala Ile Pro Leu Ala Leu Ser
    210                 215                 220

Thr Glu Ala Ile Leu His Ser Asn Asn Thr Arg Asp Met Glu Ser Asp
225                 230                 235                 240

Arg Glu Ala Gly Ile Val Thr Leu Ala Ile Leu Ile Gly Pro Thr Phe
                245                 250                 255

Ser Tyr Ile Leu Tyr Asn Thr Leu Leu Phe Leu Pro Tyr Leu Val Phe
            260                 265                 270

Ser Ile Leu Ala Thr His Cys Thr Ile Ser Leu Ala Leu Pro Leu Leu
```

```
                275                 280                 285
Thr Ile Pro Met Ala Phe Ser Leu Glu Arg Gln Phe Arg Ser Gln Ala
290                 295                 300

Phe Asn Lys Leu Pro Gln Arg Thr Ala Lys Leu Asn Leu Leu Leu Gly
305                 310                 315                 320

Leu Phe Tyr Val Phe Gly Ile Ile Leu Ala Pro Ala Gly Ser Leu Pro
                325                 330                 335

Lys Ile

<210> SEQ ID NO 25
<211> LENGTH: 338
<212> TYPE: PRT
<213> ORGANISM: Macaca mulatta

<400> SEQUENCE: 25

Met Ala Ala Ser Gln Val Leu Gly Glu Lys Ile Asn Ile Leu Ser Gly
1               5                   10                  15

Glu Thr Val Lys Ala Gly Asp Arg Glu Pro Leu Gly Asn Asp Cys Pro
                20                  25                  30

Glu Gln Asp Arg Leu Pro Gln Arg Ser Trp Arg Gln Lys Cys Ala Ser
            35                  40                  45

Tyr Val Leu Ala Leu Arg Pro Trp Ser Phe Ser Ala Ser Leu Thr Pro
        50                  55                  60

Val Ala Leu Gly Ser Ala Leu Ala Tyr Arg Ser His Gly Val Leu Asp
65                  70                  75                  80

Pro Arg Leu Leu Val Gly Cys Ala Val Ala Val Leu Ala Val His Gly
                85                  90                  95

Ala Gly Asn Leu Val Asn Thr Tyr Tyr Asp Phe Ser Lys Gly Ile Asp
                100                 105                 110

His Lys Lys Ser Asp Asp Arg Thr Leu Val Asp Arg Ile Leu Glu Pro
            115                 120                 125

Gln Asp Val Val Arg Phe Gly Val Phe Leu Tyr Thr Leu Gly Cys Val
130                 135                 140

Cys Ala Ala Cys Leu Tyr Cys Leu Ser Pro Leu Lys Leu Glu His Leu
145                 150                 155                 160

Ala Leu Ile Tyr Phe Gly Gly Leu Ser Gly Ser Phe Leu Tyr Thr Gly
                165                 170                 175

Gly Ile Gly Phe Lys Tyr Val Ala Leu Gly Asp Leu Ile Ile Leu Ile
            180                 185                 190

Thr Phe Gly Pro Leu Ala Val Met Phe Ala Tyr Ala Ile Gln Val Gly
        195                 200                 205

Ser Leu Ala Ile Phe Pro Leu Val Tyr Ala Ile Pro Leu Ala Leu Ser
210                 215                 220

Thr Glu Ala Ile Leu His Ser Asn Asn Thr Arg Asp Met Glu Ser Asp
225                 230                 235                 240

Arg Glu Ala Gly Ile Val Thr Leu Ala Ile Leu Ile Gly Pro Thr Phe
                245                 250                 255

Ser Tyr Ile Leu Tyr Asn Thr Leu Leu Phe Leu Pro Tyr Leu Val Phe
            260                 265                 270

Ser Ile Leu Ala Thr His Cys Thr Ile Ser Leu Ala Leu Pro Leu Leu
        275                 280                 285

Thr Ile Pro Met Ala Phe Ser Leu Glu Arg Gln Phe Arg Ser Gln Ala
290                 295                 300

Phe Asn Lys Leu Pro Gln Arg Thr Ala Lys Leu Asn Leu Leu Leu Gly
305                 310                 315                 320
```

```
Leu Phe Tyr Val Phe Gly Ile Ile Leu Ala Pro Ala Gly Ser Leu Pro
            325                 330                 335

Lys Leu

<210> SEQ ID NO 26
<211> LENGTH: 336
<212> TYPE: PRT
<213> ORGANISM: Mus musculus

<400> SEQUENCE: 26

Met Ala Ala Val Gln Ala Pro Gly Glu Lys Ile Asn Ile Leu Ala Gly
1               5                   10                  15

Glu Thr Ala Lys Val Gly Asp Pro Gln Lys Asn Glu Trp Pro Glu Gln
            20                  25                  30

Asp Arg Leu Pro Glu Arg Ser Trp Arg His Lys Cys Ala Ser Tyr Val
        35                  40                  45

Leu Ala Leu Arg Pro Trp Ser Phe Ser Ala Ser Leu Thr Pro Val Ala
    50                  55                  60

Leu Gly Ser Ala Leu Ala Tyr Arg Ser Gln Gly Val Leu Asp Pro Arg
65                  70                  75                  80

Leu Leu Leu Gly Cys Ala Val Ala Val Leu Ala Val His Gly Ala Gly
                85                  90                  95

Asn Leu Val Asn Thr Tyr Tyr Asp Phe Ser Lys Gly Ile Asp His Lys
            100                 105                 110

Lys Ser Asp Asp Arg Thr Leu Val Asp Arg Ile Leu Glu Pro Gln Asp
        115                 120                 125

Val Val Arg Phe Gly Val Phe Leu Tyr Thr Leu Gly Cys Val Cys Ala
    130                 135                 140

Ala Cys Leu Tyr Tyr Leu Ser Ala Leu Lys Leu Glu His Leu Ala Leu
145                 150                 155                 160

Ile Tyr Phe Gly Gly Leu Ser Gly Ser Phe Leu Tyr Thr Gly Gly Ile
                165                 170                 175

Gly Phe Lys Tyr Val Ala Leu Gly Asp Leu Val Ile Leu Ile Thr Phe
            180                 185                 190

Gly Pro Leu Ala Val Met Phe Ala Tyr Ala Val Gln Val Gly Ser Leu
        195                 200                 205

Ala Ile Phe Pro Leu Ile Tyr Ala Ile Pro Leu Ala Leu Ser Thr Glu
    210                 215                 220

Ala Ile Leu His Ser Asn Asn Thr Arg Asp Met Glu Ser Asp Arg Glu
225                 230                 235                 240

Ala Gly Ile Val Thr Leu Ala Ile Leu Ile Gly Pro Thr Phe Ser Tyr
                245                 250                 255

Val Leu Tyr Asn Thr Leu Leu Phe Val Pro Tyr Leu Ile Phe Thr Ile
            260                 265                 270

Leu Ala Thr His Cys Ser Ile Ser Leu Ala Leu Pro Leu Leu Thr Ile
        275                 280                 285

Pro Met Ala Phe Ser Leu Glu Arg Gln Phe Arg Ser Gln Ala Phe Asn
    290                 295                 300

Lys Leu Pro Gln Arg Thr Ala Lys Leu Asn Leu Leu Gly Leu Phe
305                 310                 315                 320

Tyr Val Phe Gly Ile Ile Leu Ala Pro Ala Gly Ser Leu Pro Arg Leu
                325                 330                 335

<210> SEQ ID NO 27
<211> LENGTH: 338
```

<212> TYPE: PRT
<213> ORGANISM: Rattus norvegicus

<400> SEQUENCE: 27

Met Ala Val Gln Ala Pro Gly Glu Lys Ile Asn Ile Gln Ala Gly
1               5                   10                  15

Glu Thr Thr Gln Val Gly Asp Thr Asp Gln Gln Arg Asn Asp Trp Pro
                20                  25                  30

Glu Glu Asp Arg Leu Pro Glu Arg Ser Trp Arg Gln Lys Cys Ala Ser
            35                  40                  45

Tyr Val Leu Ala Leu Arg Pro Trp Ser Phe Ser Ala Ser Leu Thr Pro
    50                  55                  60

Val Ala Leu Gly Ser Ala Leu Ala Tyr Arg Ser Gln Gly Val Leu Asp
65                  70                  75                  80

Pro Arg Leu Leu Leu Gly Cys Ala Val Ala Val Leu Ala Val His Gly
                85                  90                  95

Ala Gly Asn Leu Val Asn Thr Tyr Tyr Asp Phe Ser Lys Gly Ile Asp
                100                 105                 110

His Lys Lys Ser Asp Asp Arg Thr Leu Val Asp Arg Ile Leu Glu Pro
            115                 120                 125

Gln Asp Val Val Arg Phe Gly Val Phe Leu Tyr Thr Leu Gly Cys Val
130                 135                 140

Cys Ala Ala Tyr Leu Tyr Tyr Leu Ser Thr Leu Lys Leu Glu His Leu
145                 150                 155                 160

Ala Leu Ile Tyr Phe Gly Gly Leu Ser Gly Ser Phe Leu Tyr Thr Gly
                165                 170                 175

Gly Ile Gly Phe Lys Tyr Val Ala Leu Gly Asp Leu Val Ile Leu Ile
            180                 185                 190

Thr Phe Gly Pro Leu Ala Val Met Phe Ala Tyr Ala Val Gln Val Gly
        195                 200                 205

Ser Leu Ala Ile Phe Pro Leu Val Tyr Ala Ile Pro Leu Ala Leu Ser
210                 215                 220

Thr Glu Ala Ile Leu His Ser Asn Asn Thr Arg Asp Met Glu Ser Asp
225                 230                 235                 240

Arg Glu Ala Gly Ile Val Thr Leu Ala Ile Leu Ile Gly Pro Thr Leu
                245                 250                 255

Ser Tyr Ile Leu Tyr Asn Thr Leu Leu Phe Leu Pro Tyr Leu Ile Phe
            260                 265                 270

Thr Ile Leu Ala Thr His Cys Ser Ile Ser Leu Ala Leu Pro Leu Leu
        275                 280                 285

Thr Ser Pro Met Ala Phe Ser Leu Glu Arg Gln Phe Arg Ser Gln Ala
290                 295                 300

Phe Asn Lys Leu Pro Gln Arg Thr Ala Lys Leu Asn Leu Leu Leu Gly
305                 310                 315                 320

Leu Phe Tyr Val Phe Gly Ile Ile Leu Ala Pro Ala Gly Ser Leu Pro
                325                 330                 335

Arg Leu

<210> SEQ ID NO 28
<211> LENGTH: 337
<212> TYPE: PRT
<213> ORGANISM: Canis familiaris

<400> SEQUENCE: 28

Met Ala Ala Ser Gln Ala Ala Gly Asp Val Asn Ile Pro Ala Gly Asp
1               5                   10                  15

Ala Gly Arg Pro Gly Asp Arg Glu Pro Pro Gly Pro Asp Cys Pro Glu
            20                  25                  30

Ala Asp Arg Pro Thr Arg Arg Ser Trp Arg His Lys Cys Ala Ser Tyr
        35                  40                  45

Val Leu Ala Leu Arg Pro Trp Ser Phe Ser Ala Ser Leu Thr Pro Val
    50                  55                  60

Ala Leu Gly Ser Ala Leu Ala Tyr Arg Ala Gln Gly Gly Leu Asp Pro
65                  70                  75                  80

Arg Leu Leu Ala Gly Cys Ala Val Ala Val Leu Ala Val His Gly Ala
                85                  90                  95

Gly Asn Leu Val Asn Thr Tyr Tyr Asp Phe Ser Lys Gly Ile Asp His
            100                 105                 110

Lys Lys Ser Asp Asp Arg Thr Leu Val Asp Arg Ile Leu Glu Pro Gln
        115                 120                 125

Asp Val Val Arg Phe Gly Val Leu Leu Tyr Thr Leu Gly Cys Val Cys
    130                 135                 140

Ala Ala Gly Leu Tyr Ser Leu Ser Pro Leu Arg Leu Glu His Leu Ala
145                 150                 155                 160

Leu Ile Tyr Phe Gly Gly Leu Ser Gly Ser Phe Leu Tyr Thr Gly Gly
                165                 170                 175

Ile Gly Phe Lys Tyr Val Ala Leu Gly Asp Leu Val Ile Leu Ile Thr
            180                 185                 190

Phe Gly Pro Leu Ala Val Met Phe Ala Tyr Ala Val Gln Val Gly Ser
        195                 200                 205

Leu Ala Val Phe Pro Leu Val Tyr Ala Ile Pro Leu Ala Leu Ser Thr
    210                 215                 220

Glu Ala Ile Leu His Ser Asn Asn Thr Arg Asp Met Glu Ser Asp Arg
225                 230                 235                 240

Glu Ala Gly Ile Val Thr Leu Ala Ile Leu Ile Gly Pro Thr Leu Ser
                245                 250                 255

Tyr Met Leu Tyr Asn Thr Leu Leu Phe Leu Pro Tyr Leu Ile Phe Ser
            260                 265                 270

Ile Leu Ala Thr Arg Cys Ser Ile Ser Leu Ala Leu Pro Leu Leu Thr
        275                 280                 285

Ile Pro Met Ala Phe Ser Leu Glu Arg Gln Phe Arg Ser Gln Thr Phe
    290                 295                 300

Asn Lys Leu Pro Gln Arg Thr Ala Lys Leu Asn Leu Leu Gly Leu
305                 310                 315                 320

Phe Tyr Val Phe Gly Ile Ile Leu Ala Pro Ala Gly Ser Leu Pro Lys
                325                 330                 335

Leu

<210> SEQ ID NO 29
<211> LENGTH: 333
<212> TYPE: PRT
<213> ORGANISM: Gallus gallus

<400> SEQUENCE: 29

Met Gly Pro Ala Glu Leu Val Gln Lys Ile Ser Ile Asn Ala Glu Ser
1               5                   10                  15

Pro Arg Gly Gly Glu Arg Asn Asp Cys Gly Ala Gly Ala Glu Arg Gly
            20                  25                  30

Pro Ala Gly Gly Trp Arg Gln Lys Cys Ala Ala Tyr Val Leu Ala Leu
        35                  40                  45

```
Arg Pro Trp Ser Phe Ser Ala Ser Leu Thr Pro Val Ala Leu Gly Ser
 50                  55                  60

Ala Leu Ala Tyr Arg Ala Glu Gly Ala Leu Asp Pro Arg Leu Leu Val
 65                  70                  75                  80

Gly Ser Ala Val Ala Val Leu Ala Val His Gly Ala Gly Asn Leu Val
                 85                  90                  95

Asn Thr Tyr Tyr Asp Phe Ser Lys Gly Ile Asp His Lys Lys Ser Asp
            100                 105                 110

Asp Arg Thr Leu Val Asp Gln Ile Leu Glu Pro Gln Asp Val Val Arg
        115                 120                 125

Phe Gly Val Phe Leu Tyr Thr Val Gly Cys Ile Cys Ala Ala Gly Leu
130                 135                 140

Tyr Ala Val Ser Thr Leu Lys Leu Glu His Leu Ala Leu Val Tyr Phe
145                 150                 155                 160

Gly Gly Leu Ser Ser Ser Phe Leu Tyr Thr Gly Gly Ile Gly Phe Lys
                165                 170                 175

Tyr Val Ala Leu Gly Asp Val Val Leu Ile Thr Phe Gly Pro Leu
            180                 185                 190

Ala Val Met Phe Ala His Ala Val Gln Val Gly Tyr Leu Ser Val Ser
        195                 200                 205

Pro Leu Leu Tyr Ala Val Pro Leu Ala Leu Ser Thr Glu Ala Ile Leu
210                 215                 220

His Ser Asn Asn Thr Arg Asp Met Glu Ser Asp Gln Gln Ala Gly Ile
225                 230                 235                 240

Val Thr Leu Ala Ile Ile Gly Pro Ala Phe Ser Tyr Val Leu Tyr
                245                 250                 255

Thr Val Leu Leu Phe Leu Pro Tyr Leu Ile Phe Cys Val Leu Ala Thr
            260                 265                 270

Arg Tyr Thr Ile Ser Met Ala Leu Pro Leu Leu Thr Ile Pro Met Ala
        275                 280                 285

Phe Ser Leu Glu Arg Gln Phe Arg Ser Gln Asn Phe Asn Lys Ile Pro
290                 295                 300

Gln Arg Thr Ala Lys Leu Asn Leu Leu Leu Gly Leu Phe Tyr Val Phe
305                 310                 315                 320

Gly Ile Met Leu Ala Pro Ala Gly Ala Leu Pro Lys Leu
                325                 330

<210> SEQ ID NO 30
<211> LENGTH: 345
<212> TYPE: PRT
<213> ORGANISM: Silurana tropicalis

<400> SEQUENCE: 30

Met Lys Pro Asp Asp Cys Leu Asn Asn Ile His Ile Glu Thr Glu Asn
1               5                   10                  15

Leu Asp Glu Val Asp Leu Thr Lys Leu Thr Gly Glu Ala His Ser Leu
            20                  25                  30

Ser Asn Gly Ile Val Pro Pro Phe Thr Asp Lys Thr Phe Arg Lys Ala
        35                  40                  45

Thr Ser Phe Lys Gln Lys Cys Ala Thr Tyr Val Leu Ala Leu Arg Pro
 50                  55                  60

Trp Ser Phe Ser Ala Ser Leu Ile Pro Val Ala Leu Gly Thr Ala Ile
 65                  70                  75                  80

Ala Tyr Arg Ser Gly Gly Ser Leu Asp Leu Leu Leu Phe Val Val Cys
                 85                  90                  95
```

```
Ala Val Ala Val Leu Ala Val His Gly Ala Gly Asn Leu Val Asn Thr
            100                 105                 110

Tyr Tyr Asp Phe Ser Lys Gly Ile Asp His Lys Lys Ser Asp Asp Arg
        115                 120                 125

Thr Leu Val Asp His Ile Leu Glu Pro Gln Asp Val Val Arg Phe Gly
130                 135                 140

Val Phe Leu Tyr Thr Leu Gly Cys Leu Cys Ala Ala Cys Leu Tyr Phe
145                 150                 155                 160

Ile Ser Lys Leu Lys Leu Glu His Leu Ala Leu Ile Tyr Phe Gly Gly
                165                 170                 175

Leu Ser Ser Ser Phe Leu Tyr Thr Gly Ile Gly Phe Lys Tyr Val
            180                 185                 190

Ala Leu Gly Asp Leu Val Ile Leu Ile Thr Phe Gly Pro Leu Ala Val
            195                 200                 205

Met Phe Ala His Ala Val Gln Val Gly Tyr Leu Ala Val Thr Pro Leu
    210                 215                 220

Leu Tyr Ala Val Pro Leu Ala Leu Ser Thr Glu Ala Ile Leu His Ser
225                 230                 235                 240

Asn Asn Thr Arg Asp Met Glu Ser Asp Arg Gln Ala Gly Ile Val Thr
                245                 250                 255

Leu Ala Ile Leu Val Gly Pro Met Phe Ser Tyr Met Leu Tyr Asn Leu
            260                 265                 270

Leu Val Phe Leu Pro Tyr Leu Ile Phe Ser Ile Leu Ala Thr Arg Tyr
        275                 280                 285

Thr Ile Ser Met Ala Leu Pro Leu Leu Thr Ile Pro Leu Ala Phe Ser
290                 295                 300

Leu Glu Arg Gln Phe Arg Ser Gln Asn Phe Asn Lys Ile Pro Gln Arg
305                 310                 315                 320

Thr Ala Lys Leu Asn Leu Leu Val Gly Leu Phe Tyr Val Phe Gly Ile
                325                 330                 335

Val Leu Ala Pro Ala Gly Ser Leu Pro
            340                 345

<210> SEQ ID NO 31
<211> LENGTH: 359
<212> TYPE: PRT
<213> ORGANISM: Drosophila melanogaster

<400> SEQUENCE: 31

Met Ala Thr Ser Ser Gln Leu Leu Pro Asn Gly Asn Leu Ser Arg Asn
1               5                   10                  15

Gly Lys Thr Lys Thr Glu Asp Gly Glu Glu Val Glu Ala Val Val Gly
            20                  25                  30

Ala Arg Ala Ala Gly Ala Asp Ala Gly Val Ala Leu Thr Gly Arg Leu
        35                  40                  45

Thr Gly His Pro Ser Thr Ser Gly Thr Phe Met Lys Leu Lys Thr Tyr
    50                  55                  60

Leu Leu Ala Leu Arg Pro Trp Ser Leu Ser Ala Ser Leu Val Pro Thr
65                  70                  75                  80

Leu Leu Gly Ser Ala Leu Ala Tyr Arg Ser Gln Trp Ala Glu Glu Phe
                85                  90                  95

Ser Leu Ala Thr Phe Phe Leu Thr Ala Phe Thr Val Thr Val His
            100                 105                 110

Cys Ala Gly Asn Val Val Asn Thr Tyr Phe Asp Phe Ile Lys Gly Ile
        115                 120                 125
```

Asp Lys Gln Lys Ala Asp Asp Arg Thr Leu Val Asp His Ile Leu Thr
            130                 135                 140

Lys Asp Glu Val Val Ser Leu Gly Ala Ile Leu Tyr Met Ala Gly Cys
145                 150                 155                 160

Gly Gly Phe Val Leu Leu Ala Val Leu Ser Pro Ala Lys Met Glu His
                165                 170                 175

Leu Ala Leu Ile Tyr Phe Gly Gly Leu Ser Ser Phe Leu Tyr Thr
            180                 185                 190

Gly Gly Ile Gly Phe Lys Tyr Ile Ala Leu Gly Asp Leu Val Ile Leu
            195                 200                 205

Ile Leu Phe Gly Pro Ile Ser Val Leu Phe Ala Phe Met Ser Gln Thr
            210                 215                 220

Gly His Leu Asp Trp Thr Thr Met Gly Tyr Ala Ile Pro Leu Ala Leu
225                 230                 235                 240

Asn Thr Glu Ala Ile Leu His Ser Asn Asn Thr Arg Asp Ala Asp Asn
                245                 250                 255

Asp Arg Arg Ala Gly Ile Val Thr Leu Ala Ile Leu Ile Gly Arg Thr
                260                 265                 270

Ala Ser His Val Leu Tyr Ala Met Leu Leu Phe Ala Pro Tyr Ser Leu
                275                 280                 285

Phe Phe Ile Phe Gly Leu Lys Tyr Ser Leu Trp Phe Leu Leu Pro Leu
            290                 295                 300

Val Thr Leu Pro Gln Ala Phe Gln Ile Glu Lys Arg Phe Arg Asn Glu
305                 310                 315                 320

Gln Thr Met His Leu Val Pro Arg Gln Thr Ala Lys Leu Asn Phe Phe
                325                 330                 335

Phe Gly Ile Leu Tyr Val Val Ala Cys Cys Cys Ala His Gln Leu Pro
            340                 345                 350

Thr Phe Gly Leu Arg Arg Asn
            355

<210> SEQ ID NO 32
<211> LENGTH: 299
<212> TYPE: PRT
<213> ORGANISM: Anopheles gambiae

<400> SEQUENCE: 32

Leu Met Lys Phe Lys Thr Tyr Leu Ser Ala Leu Arg Pro Trp Ser Leu
1               5                   10                  15

Ser Ala Ser Leu Ile Pro Thr Leu Leu Gly Thr Ala Leu Ala Cys Glu
            20                  25                  30

Ser Gly Tyr Glu His Leu Ser Phe Phe Thr Phe Leu Cys Thr Val Leu
            35                  40                  45

Thr Val Val Thr Val His Cys Ala Gly Asn Val Val Asn Thr Tyr Tyr
50                  55                  60

Asp Phe Val Lys Gly Ile Asp Asp Arg Lys Ala Asp Asp Arg Thr Leu
65                  70                  75                  80

Val Asp His Ile Leu Ser Gln Asp Glu Val Val Thr Leu Gly Val Leu
                85                  90                  95

Leu Tyr Gly Ala Gly Cys Leu Gly Phe Val Cys Leu Val Tyr Leu Ser
                100                 105                 110

Pro Ala Arg Leu Glu His Leu Ala Leu Val Phe Phe Gly Gly Leu Ser
            115                 120                 125

Ser Ser Phe Leu Tyr Thr Gly Gly Phe Gly Leu Lys Tyr Ile Ala Leu
    130                 135                 140

```
Gly Asp Val Leu Val Leu Val Ile Phe Gly Pro Ile Ser Val Leu Phe
145                 150                 155                 160

Ser Tyr Met Ala Gln Thr Gly Arg Tyr Glu Trp Ala Thr Ile Phe Tyr
            165                 170                 175

Ala Ile Pro Leu Ala Leu Asn Thr Glu Ala Ile Leu His Ser Asn Asn
        180                 185                 190

Thr Arg Asp Ala Glu Ser Asp Lys Arg Val Gly Ile Val Thr Leu Ala
    195                 200                 205

Ile Leu Ile Gly Arg Thr Gly Ser Tyr Ile Leu Tyr Gly Val Leu Leu
210                 215                 220

Phe Thr Pro Tyr Val Ile Phe Val Val Leu Gly Met Lys Tyr Ser Ala
225                 230                 235                 240

Leu Phe Leu Leu Pro Met Val Thr Phe Lys Gln Ala Phe Ala Leu Glu
                245                 250                 255

Arg Gln Phe Arg Asn Glu Ser Thr Met Gln Met Val Pro Arg Gln Thr
            260                 265                 270

Ala Lys Leu Asn Leu Phe Phe Gly Ile Leu Tyr Val Val Ala Cys Phe
        275                 280                 285

Gly Ala Pro Gln Leu Pro Phe Ile Thr Arg Lys
    290                 295
```

<210> SEQ ID NO 33
<211> LENGTH: 15
<212> TYPE: DNA
<213> ORGANISM: Homo sapiens

<400> SEQUENCE: 33
cacgtaccgc gcccg     15

<210> SEQ ID NO 34
<211> LENGTH: 15
<212> TYPE: DNA
<213> ORGANISM: Homo sapiens

<400> SEQUENCE: 34
ataatactaa aatcg     15

<210> SEQ ID NO 35
<211> LENGTH: 15
<212> TYPE: DNA
<213> ORGANISM: Homo sapiens

<400> SEQUENCE: 35
tttccgtaac tagta     15

<210> SEQ ID NO 36
<211> LENGTH: 16
<212> TYPE: DNA
<213> ORGANISM: Homo sapiens

<400> SEQUENCE: 36
atcgtttccg taacta    16

<210> SEQ ID NO 37
<211> LENGTH: 18
<212> TYPE: DNA
<213> ORGANISM: Homo sapiens

<400> SEQUENCE: 37
gtaccgcgcc cgttggac   18

```
<210> SEQ ID NO 38
<211> LENGTH: 17
<212> TYPE: DNA
<213> ORGANISM: Homo sapiens

<400> SEQUENCE: 38
accacttgtg gataata                                                  17

<210> SEQ ID NO 39
<211> LENGTH: 12
<212> TYPE: DNA
<213> ORGANISM: Homo sapiens

<400> SEQUENCE: 39
taagacgtat cg                                                       12

<210> SEQ ID NO 40
<211> LENGTH: 12
<212> TYPE: DNA
<213> ORGANISM: Homo sapiens

<400> SEQUENCE: 40
ggcgctatac ct                                                       12

<210> SEQ ID NO 41
<211> LENGTH: 12
<212> TYPE: DNA
<213> ORGANISM: Homo sapiens

<400> SEQUENCE: 41
gcgcttcgcc cg                                                       12

<210> SEQ ID NO 42
<211> LENGTH: 16
<212> TYPE: DNA
<213> ORGANISM: Homo sapiens

<400> SEQUENCE: 42
acgtatcgtc gttgtg                                                   16

<210> SEQ ID NO 43
<211> LENGTH: 18
<212> TYPE: DNA
<213> ORGANISM: Homo sapiens

<400> SEQUENCE: 43 ataccttcg ctagcgct                                                  18

<210> SEQ ID NO 44
<211> LENGTH: 16
<212> TYPE: DNA
<213> ORGANISM: Homo sapiens

<400> SEQUENCE: 44
gctagcgctt cgcccg                                                   16

<210> SEQ ID NO 45
<211> LENGTH: 18
<212> TYPE: DNA
<213> ORGANISM: Homo sapiens

<400> SEQUENCE: 45
cggaaccgaa ggaaggtc                                                 18
```

```
<210> SEQ ID NO 46
<211> LENGTH: 20
<212> TYPE: DNA
<213> ORGANISM: Homo sapiens

<400> SEQUENCE: 46
ccaagattcg gtccacaagt                                               20

<210> SEQ ID NO 47
<211> LENGTH: 18
<212> TYPE: DNA
<213> ORGANISM: Homo sapiens

<400> SEQUENCE: 47
ggctcttggt gggttgtg                                                 18

<210> SEQ ID NO 48
<211> LENGTH: 22
<212> TYPE: DNA
<213> ORGANISM: Homo sapiens

<400> SEQUENCE: 48
aaagcggctt aaattagaaa gc                                            22

<210> SEQ ID NO 49
<211> LENGTH: 19
<212> TYPE: DNA
<213> ORGANISM: Homo sapiens

<400> SEQUENCE: 49
aagtggcctg cctcttcac                                                19

<210> SEQ ID NO 50
<211> LENGTH: 19
<212> TYPE: DNA
<213> ORGANISM: Homo sapiens

<400> SEQUENCE: 50
gctgatggtg cagtgtgtg                                                19

<210> SEQ ID NO 51
<211> LENGTH: 19
<212> TYPE: DNA
<213> ORGANISM: Homo sapiens

<400> SEQUENCE: 51
gggaggctgg tatcgtcac                                                19

<210> SEQ ID NO 52
<211> LENGTH: 20
<212> TYPE: DNA
<213> ORGANISM: Homo sapiens

<400> SEQUENCE: 52
tgactgccaa atcacattcc                                               20

<210> SEQ ID NO 53
<211> LENGTH: 20
<212> TYPE: DNA
<213> ORGANISM: Homo sapiens

<400> SEQUENCE: 53
caactcattt ccagggcttt                                               20
```

-continued

```
<210> SEQ ID NO 54
<211> LENGTH: 27
<212> TYPE: DNA
<213> ORGANISM: Homo sapiens

<400> SEQUENCE: 54
gtttcttgtg gtccatagac cccacag                                          27

<210> SEQ ID NO 55
<211> LENGTH: 20
<212> TYPE: DNA
<213> ORGANISM: Homo sapiens

<400> SEQUENCE: 55
cacacctttc cttcgtccat                                                  20

<210> SEQ ID NO 56
<211> LENGTH: 28
<212> TYPE: DNA
<213> ORGANISM: Homo sapiens

<400> SEQUENCE: 56
gtttcttttc aaggggtag tagggagt                                          28

<210> SEQ ID NO 57
<211> LENGTH: 20
<212> TYPE: DNA
<213> ORGANISM: Homo sapiens

<400> SEQUENCE: 57
aagtctggac actcccctga                                                  20

<210> SEQ ID NO 58
<211> LENGTH: 27
<212> TYPE: DNA
<213> ORGANISM: Homo sapiens

<400> SEQUENCE: 58
gtttctttaa ggccagcagt cctcatc                                          27

<210> SEQ ID NO 59
<211> LENGTH: 22
<212> TYPE: DNA
<213> ORGANISM: Homo sapiens

<400> SEQUENCE: 59
tgggagagag agaatgaatg tg                                               22

<210> SEQ ID NO 60
<211> LENGTH: 27
<212> TYPE: DNA
<213> ORGANISM: Homo sapiens

<400> SEQUENCE: 60
gtttcttgag gtcgaaggga aaagagg                                          27

<210> SEQ ID NO 61
<211> LENGTH: 20
<212> TYPE: DNA
<213> ORGANISM: Homo sapiens

<400> SEQUENCE: 61
tctccttgct gccctagttt                                                  20
```

```
<210> SEQ ID NO 62
<211> LENGTH: 26
<212> TYPE: DNA
<213> ORGANISM: Homo sapiens

<400> SEQUENCE: 62
gtttcttctc ctttccccca tgtcag                                    26

<210> SEQ ID NO 63
<211> LENGTH: 21
<212> TYPE: DNA
<213> ORGANISM: Homo sapiens

<400> SEQUENCE: 63
ttggggcaaa tacaatgaaa a                                         21

<210> SEQ ID NO 64
<211> LENGTH: 27
<212> TYPE: DNA
<213> ORGANISM: Homo sapiens

<400> SEQUENCE: 64
gtttcttttc ctcaccatcc tttcctg                                   27

<210> SEQ ID NO 65
<211> LENGTH: 25
<212> TYPE: DNA
<213> ORGANISM: Homo sapiens

<400> SEQUENCE: 65
actaacttgt cccagattac tgtgt                                     25

<210> SEQ ID NO 66
<211> LENGTH: 27
<212> TYPE: DNA
<213> ORGANISM: Homo sapiens

<400> SEQUENCE: 66
gtttcttggc aacaaaggga gactctg                                   27

<210> SEQ ID NO 67
<211> LENGTH: 22
<212> TYPE: DNA
<213> ORGANISM: Homo sapiens

<400> SEQUENCE: 67
cggtggaatt tagaagccta tg                                        22

<210> SEQ ID NO 68
<211> LENGTH: 28
<212> TYPE: DNA
<213> ORGANISM: Homo sapiens

<400> SEQUENCE: 68
gtttcttcct gaatgatgtt ccctttca                                  28

<210> SEQ ID NO 69
<211> LENGTH: 21
<212> TYPE: DNA
<213> ORGANISM: Homo sapiens

<400> SEQUENCE: 69
tcgcaagtag aaggttttgg a                                         21
```

```
<210> SEQ ID NO 70
<211> LENGTH: 27
<212> TYPE: DNA
<213> ORGANISM: Homo sapiens

<400> SEQUENCE: 70
gtttctttgc accactagga ggctaca                                         27

<210> SEQ ID NO 71
<211> LENGTH: 19
<212> TYPE: DNA
<213> ORGANISM: Homo sapiens

<400> SEQUENCE: 71
gtgggaggat tgcttgagg                                                  19

<210> SEQ ID NO 72
<211> LENGTH: 29
<212> TYPE: DNA
<213> ORGANISM: Homo sapiens

<400> SEQUENCE: 72
gtttctttgc ttagcaaaag ctatccaaa                                       29

<210> SEQ ID NO 73
<211> LENGTH: 18
<212> TYPE: DNA
<213> ORGANISM: Homo sapiens

<400> SEQUENCE: 73
acctagcagg cggaggtt                                                   18

<210> SEQ ID NO 74
<211> LENGTH: 34
<212> TYPE: DNA
<213> ORGANISM: Homo sapiens

<400> SEQUENCE: 74
gtttctttgg tgatactaaa aactgtatgc aaag                                 34

<210> SEQ ID NO 75
<211> LENGTH: 19
<212> TYPE: DNA
<213> ORGANISM: Homo sapiens

<400> SEQUENCE: 75
catgtggcct aacaaaagg                                                  19

<210> SEQ ID NO 76
<211> LENGTH: 27
<212> TYPE: DNA
<213> ORGANISM: Homo sapiens

<400> SEQUENCE: 76
gtttcttaaa aacaaaggtg cctggtg                                         27

<210> SEQ ID NO 77
<211> LENGTH: 20
<212> TYPE: DNA
<213> ORGANISM: Homo sapiens

<400> SEQUENCE: 77
cagggagctc tgtgtttgaa                                                 20
```

```
<210> SEQ ID NO 78
<211> LENGTH: 27
<212> TYPE: DNA
<213> ORGANISM: Homo sapiens

<400> SEQUENCE: 78
gtttcttacc taatgaacgg gcaacag                                          27

<210> SEQ ID NO 79
<211> LENGTH: 20
<212> TYPE: DNA
<213> ORGANISM: Homo sapiens

<400> SEQUENCE: 79
aatctctgtt ccccagcaac                                                  20

<210> SEQ ID NO 80
<211> LENGTH: 27
<212> TYPE: DNA
<213> ORGANISM: Homo sapiens

<400> SEQUENCE: 80
gtttcttggg cagcctgaca tacctac                                          27

<210> SEQ ID NO 81
<211> LENGTH: 22
<212> TYPE: DNA
<213> ORGANISM: Homo sapiens

<400> SEQUENCE: 81
cggggaaatc caatacgctg aa                                               22

<210> SEQ ID NO 82
<211> LENGTH: 27
<212> TYPE: DNA
<213> ORGANISM: Homo sapiens

<400> SEQUENCE: 82
gtttcttccg tctctcttgc tgtcctc                                          27

<210> SEQ ID NO 83
<211> LENGTH: 20
<212> TYPE: DNA
<213> ORGANISM: Homo sapiens

<400> SEQUENCE: 83
atgtccggga atcaacacac                                                  20

<210> SEQ ID NO 84
<211> LENGTH: 27
<212> TYPE: DNA
<213> ORGANISM: Homo sapiens

<400> SEQUENCE: 84
gtttcttgaa ctgccctgga atgaact                                          27

<210> SEQ ID NO 85
<211> LENGTH: 20
<212> TYPE: DNA
<213> ORGANISM: Homo sapiens

<400> SEQUENCE: 85
tccccaaaac tctctcctca                                                  20
```

```
<210> SEQ ID NO 86
<211> LENGTH: 27
<212> TYPE: DNA
<213> ORGANISM: Homo sapiens

<400> SEQUENCE: 86
gtttcttcag gacctcacag ctcttgg                                27

<210> SEQ ID NO 87
<211> LENGTH: 20
<212> TYPE: DNA
<213> ORGANISM: Homo sapiens

<400> SEQUENCE: 87
aggacctgac cctgagacct                                        20

<210> SEQ ID NO 88
<211> LENGTH: 27
<212> TYPE: DNA
<213> ORGANISM: Homo sapiens

<400> SEQUENCE: 88
gtttcttagc tctgagccat tcgagag                                27

<210> SEQ ID NO 89
<211> LENGTH: 22
<212> TYPE: DNA
<213> ORGANISM: Homo sapiens

<400> SEQUENCE: 89
tgtctgtcca acaagaagat gc                                     22

<210> SEQ ID NO 90
<211> LENGTH: 27
<212> TYPE: DNA
<213> ORGANISM: Homo sapiens

<400> SEQUENCE: 90
gtttcttatt gaagccaggc tgagagg                                27

<210> SEQ ID NO 91
<211> LENGTH: 20
<212> TYPE: DNA
<213> ORGANISM: Homo sapiens

<400> SEQUENCE: 91
ttcagcatca tgtggtttgg                                        20

<210> SEQ ID NO 92
<211> LENGTH: 28
<212> TYPE: DNA
<213> ORGANISM: Homo sapiens

<400> SEQUENCE: 92
gtttcttttt cccctatgtg acagcatc                               28

<210> SEQ ID NO 93
<211> LENGTH: 20
<212> TYPE: DNA
<213> ORGANISM: Homo sapiens

<400> SEQUENCE: 93
tgttgactgt ctggccatct                                        20
```

```
<210> SEQ ID NO 94
<211> LENGTH: 27
<212> TYPE: DNA
<213> ORGANISM: Homo sapiens

<400> SEQUENCE: 94
gtttcttagg gctcagagag gagctgt                                    27

<210> SEQ ID NO 95
<211> LENGTH: 20
<212> TYPE: DNA
<213> ORGANISM: Homo sapiens

<400> SEQUENCE: 95
ttatcccacc gctttctctg                                            20

<210> SEQ ID NO 96
<211> LENGTH: 27
<212> TYPE: DNA
<213> ORGANISM: Homo sapiens

<400> SEQUENCE: 96
gtttcttgaa atggaggagg ggaaaat                                    27

<210> SEQ ID NO 97
<211> LENGTH: 20
<212> TYPE: DNA
<213> ORGANISM: Homo sapiens

<400> SEQUENCE: 97
cagactccca agcacagaca                                            20

<210> SEQ ID NO 98
<211> LENGTH: 27
<212> TYPE: DNA
<213> ORGANISM: Homo sapiens

<400> SEQUENCE: 98
gtttcttgtc ccctggcagg tgtagta                                    27

<210> SEQ ID NO 99
<211> LENGTH: 20
<212> TYPE: DNA
<213> ORGANISM: Homo sapiens

<400> SEQUENCE: 99
ccagcgctgt acctaagctg                                            20

<210> SEQ ID NO 100
<211> LENGTH: 27
<212> TYPE: DNA
<213> ORGANISM: Homo sapiens

<400> SEQUENCE: 100
gtttcttcca cttgggtgtc tgtgcat                                    27

<210> SEQ ID NO 101
<211> LENGTH: 20
<212> TYPE: DNA
<213> ORGANISM: Homo sapiens

<400> SEQUENCE: 101
caaacaagac cccaaaccag                                            20
```

<210> SEQ ID NO 102
<211> LENGTH: 27
<212> TYPE: DNA
<213> ORGANISM: Homo sapiens

<400> SEQUENCE: 102
gtttcttggg ggtgagtagc tcttctg                                27

<210> SEQ ID NO 103
<211> LENGTH: 20
<212> TYPE: DNA
<213> ORGANISM: Homo sapiens

<400> SEQUENCE: 103
caaacaagac cccaaaccag                                        20

<210> SEQ ID NO 104
<211> LENGTH: 28
<212> TYPE: DNA
<213> ORGANISM: Homo sapiens

<400> SEQUENCE: 104
gtttcttgct cagagagggg tctgaact                               28

<210> SEQ ID NO 105
<211> LENGTH: 20
<212> TYPE: DNA
<213> ORGANISM: Homo sapiens

<400> SEQUENCE: 105
ccaggacctc ctgacttgac                                        20

<210> SEQ ID NO 106
<211> LENGTH: 27
<212> TYPE: DNA
<213> ORGANISM: Homo sapiens

<400> SEQUENCE: 106
gtttcttctg ctaggctgga tgctaca                                27

<210> SEQ ID NO 107
<211> LENGTH: 19
<212> TYPE: DNA
<213> ORGANISM: Homo sapiens

<400> SEQUENCE: 107
agactcccag ggtcgtcag                                         19

<210> SEQ ID NO 108
<211> LENGTH: 27
<212> TYPE: DNA
<213> ORGANISM: Homo sapiens

<400> SEQUENCE: 108
gtttcttgag gtcgctcctg gatgtag                                27

<210> SEQ ID NO 109
<211> LENGTH: 19
<212> TYPE: DNA
<213> ORGANISM: Homo sapiens

<400> SEQUENCE: 109
cggtctgaga agcttcagg                                         19

```
<210> SEQ ID NO 110
<211> LENGTH: 26
<212> TYPE: DNA
<213> ORGANISM: Homo sapiens

<400> SEQUENCE: 110
gtttcttcag aaagtgcgca gagtgg                                          26

<210> SEQ ID NO 111
<211> LENGTH: 23
<212> TYPE: DNA
<213> ORGANISM: Homo sapiens

<400> SEQUENCE: 111
tggttctcat atacctgctt tgc                                             23

<210> SEQ ID NO 112
<211> LENGTH: 25
<212> TYPE: DNA
<213> ORGANISM: Homo sapiens

<400> SEQUENCE: 112
gtttcttgct ggggcgacag agcta                                           25

<210> SEQ ID NO 113
<211> LENGTH: 20
<212> TYPE: DNA
<213> ORGANISM: Homo sapiens

<400> SEQUENCE: 113
agaagtttcg gtgagccaag                                                 20

<210> SEQ ID NO 114
<211> LENGTH: 27
<212> TYPE: DNA
<213> ORGANISM: Homo sapiens

<400> SEQUENCE: 114
gtttcttctc ctcactggct tggaaac                                         27

<210> SEQ ID NO 115
<211> LENGTH: 20
<212> TYPE: DNA
<213> ORGANISM: Homo sapiens

<400> SEQUENCE: 115
accttcagct tcggtctcct                                                 20

<210> SEQ ID NO 116
<211> LENGTH: 27
<212> TYPE: DNA
<213> ORGANISM: Homo sapiens

<400> SEQUENCE: 116
gtttcttgtg agggtggaga gttcagc                                         27

<210> SEQ ID NO 117
<211> LENGTH: 22
<212> TYPE: DNA
<213> ORGANISM: Homo sapiens

<400> SEQUENCE: 117
tgggtgggta agggctgtgt aa                                              22
```

```
<210> SEQ ID NO 118
<211> LENGTH: 27
<212> TYPE: DNA
<213> ORGANISM: Homo sapiens

<400> SEQUENCE: 118
gtttcttggt gctggttgat gaatcct                                              27

<210> SEQ ID NO 119
<211> LENGTH: 18
<212> TYPE: DNA
<213> ORGANISM: Homo sapiens

<400> SEQUENCE: 119
cacctgcata gggccatc                                                        18

<210> SEQ ID NO 120
<211> LENGTH: 28
<212> TYPE: DNA
<213> ORGANISM: Homo sapiens

<400> SEQUENCE: 120
gtttcttccc tccctctgtt aaccatgt                                             28

<210> SEQ ID NO 121
<211> LENGTH: 21
<212> TYPE: DNA
<213> ORGANISM: Homo sapiens

<400> SEQUENCE: 121
tgctggagtt caagagcctg t                                                    21

<210> SEQ ID NO 122
<211> LENGTH: 27
<212> TYPE: DNA
<213> ORGANISM: Homo sapiens

<400> SEQUENCE: 122
gtttcttggc ctcactacct gaacctg                                              27
```

MUTATIONS IN HUMAN UBIAD1

CLAIM OF PRIORITY

This application hereby claims the benefit of U.S. provisional patent application Ser. Nos. 60/899,726, which was filed on Feb. 6, 2007; and 60/921,899, which was filed on Apr. 5, 2007, each of which is hereby incorporated by reference.

BRIEF DESCRIPTION OF THE INVENTION

The invention relates to nucleotide sequences for human UBIAD1 and polypeptides encoded by the nucleotide sequences. The invention also relates to the identification of human gene UBIAD1 as causal for Schnyder Corneal Dystrophy.

BACKGROUND

Schnyder crystalline corneal dystrophy (SCCD, OMIM 121800) is a rare inherited disorder for which the most prominent feature is progressive, bilateral corneal clouding in the eyes of affected individuals. Although this can appear as early as the first decade of life, it more commonly occurs in the late teens. Thereafter, the clinical course is somewhat variable, although reduced vision (particularly under brightly lit conditions) usually mandates intervention in the fourth or fifth decades of life. Phototherapeutic keratectomy (a procedure similar to that used in laser vision correction) can be temporarily useful in selected cases, but the definitive treatment is corneal transplantation. SCCD affects both sexes equally, and is found in multiple ethnic groups around the globe.

Pathophysiologically, SCCD appears to result from an abnormality in lipid metabolism in the cells of the cornea, and perhaps elsewhere in the body. Pathologic examination of corneal tissue removed from affected patients during transplantation surgery has revealed a tenfold increase in local cholesterol levels, and a fivefold increase in phospholipids. Immunohistochemical analysis of the same tissue is consistent with an underlying defect in HDL metabolism. SCCD has also been linked to increased serum cholesterol and thus, to an elevated risk of cardiovascular events such as myocardial infarction (heart attack) and stroke.

Although SCCD appears strongly genetic, identification of a causal gene has been elusive. Shearman et al. performed linkage analysis on a large family originally of Swedish/Finnish ancestry, localizing the defective gene to the short arm of chromosome 1, at 1p34-36 (*Hum Mol Genet* 5:1667-1672 (1996)). Theendakara et al. further narrowed the SCCD locus, reducing the candidate region to a 1.58 Mbp (million base pair) interval lying between genetic markers D1S244 and D1S3153 (*Hum Genet* 114:594-600 (2004)). Recently, Aldave et al. sequenced 15 of the 31 positional candidate genes within this region, finding no pathogenic mutations and tentatively excluding them as causing SCCD (*Mol Vis* 11:713-716 (2005)).

According to the NCBI genome database, UBIAD1 encodes a protein of 338 amino acids. UBIAD1 is a highly conserved gene, almost 100% identical across much of its length in vertebrate genomes and with extensive homology in insects. InterPro, Pfam and ProSite predict that UBIAD1 contains a prenyltransferase domain from residues 58-333, for which the archetype is bacterial protein UbiA. PSORTII predicts 7 transmembrane domains and integral membrane localization. Multiple transmembrane helices are also predicted by HMMTOP, TMPRED, TOPPRED and TMM. No signal peptide or cleavage signal is predicted by SignalP. The probability of mitochondrial targetting is unlikely (0.14) according to MITOPROT. The protein is not predicted to have a peroxisomal targeting signal 1 motif by PTS1. No potential GPI-modification site was predicted by bigPI or DGPI. No myristoylation site was predicted by NMT. No PEST domains were predicted by PESTfind. No prenylation sites were predicted by PrePS.

UBIAD1 is ubiquitously expressed; however the eye has been identified to have the highest normalized expression distribution of the 39 tissues reported at the Source (//genome-www5.Stanford) and of the 49 tissues identified at the Expression Profile Viewer (//www.ncbi.nlm/nih.gov).

McGarvey et al. reported two UBIAD1 transcripts of ~1.5 and ~3.5 kb (*Oncogene* 20:1042-1051 (2001)). The 1.5 kb transcript is attributable to the 1520 bp UBIAD1 reference sequence in NCBI (NM-013319.1) and Ensembl (Build 38) coding for a 338 amino acid protein. The 3.5 kb transcript identified by McGarvey et al. corresponds to the Ensembl (Build 38) gene predictions 3646 bp ENST00000376810. Also identified is a 3140 bp Ensembl (Build 38) gene predictions ENST00000240179 and NCBI cDNA clone AK074890. There is a rare variant that is predicted to splice out the UBIAD1 second exon and add three additional amino acids to the 3'end of exon 1 (Ensembl ENST00000376804; Expasy Q9Y5Z9-2). These additional 3 amino acids are derived from a putative ubiquitin-conjugating enzyme E2 variant 2 (UBE2V2) pseudogene that is approximately 8.6 kb from the 3' UBIAD1 second exon (NCBI Accession AL031291).

SUMMARY OF THE INVENTION

In general, the invention provides polynucleotides and polypeptides which encode UBIAD 1. The invention also provides antibodies that bind to the polypeptide and a method of screening for modulators of the putative UBIAD1 active site. The invention is also related to UBIAD1 and more specifically to five different mutations in UBIAD1 which are putatively causal for SCD. The mutations, numbered in reference to the wildtype amino acid sequence (SEQ ID NO: 18) beginning at the amino-terminal end of the protein, are 1) amino-acid 102 asparagine-to-serine (SEQ ID NOs: 1, 2 and 19); 2) amino-acid 112 aspartic acid-to-glycine (SEQ ID NOs: 3, 4 and 20); 3) amino-acid 119 arginine-to-glycine (SEQ ID NOs: 5, 6 and 21); 4) amino acid 175 threonine-to-isoleucine (SEQ ID NOs: 7, 8 and 22), and 5) amino acid 232 asparagine-to-serine (SEQ ID NOs: 9, 10 and 23).

In a one aspect, the invention provides an isolated polynucleotide encoding an amino acid sequence as set forth in SEQ ID NOs: 2, 4, 6, 8, 10 or 12. The isolated polynucleotide can be SEQ ID NO: 19, 20, 21, 22, 23 or 11; SEQ ID NOs: 19, 20, 21, 22, 23 or 11 where T can also be U; a nucleotide sequence complementary to SEQ ID NOs: 19, 20, 21, 22, 23 or 11; and fragments of SEQ ID NOs: 19, 20, 21, 22, 23 or 11 that are at least 10 bases in length and hybridize under stringent conditions to DNA that encodes the polypeptide of SEQ ID NOs: 2, 4, 6, 8, 10 or 12.

In another aspect, the invention provides vectors comprising nucleic acids of SEQ ID NOs. 19, 20, 21, 22, 23 and 11.

In another aspect, the invention provides a host cell with a vector comprising nucleic acids of SEQ ID NOs. 19, 20, 21, 22, 23 and 11.

In another aspect, the invention provides an isolated polynucleotide comprising at least 10 nucleotides, said nucleic acid molecule comprising a nucleotide sequence complementary to at least a portion of a sequence of SEQ ID NOs: 13 or 15.

In another aspect, the invention provides an oligonucleotide probe that hybridizes under stringent conditions to the sequence of SEQ ID NOs: 13 or 15. Examples of such probes are provided as SEQ ID NOs: 33 through 44.

In another aspect, the invention provides an isolated polypeptide encoded by the polynucleotide of SEQ ID NOs: 19, 20, 21, 22, 23 or 11. The polypeptide can be SEQ ID NOs: 2, 4, 6, 8, 10 or 12.

In another aspect, the invention provides an isolated fragment of a polypeptide comprising SEQ ID NOs: 14 or 16.

In another aspect, the invention provides a method of screening for modulators of SEQ ID NOs: 14 or 16.

In another aspect, the invention provides an antibody that binds to the polypeptide of SEQ ID NOs: 2, 4, 6, 8, 10 or 12, 14 or 16.

BRIEF DESCRIPTION OF THE DRAWINGS

FIG. 1. depicts the alignment of human UBIAD1 with vertebrate putative orthologs and invertebrate homologs, with mutations identified above the conserved sequences. Based on the RefSeq annotated protein sequence, mutations are found at amino acid 102 N-to-S (SEQ ID NO: 2); amino acid 112 D-to-G (SEQ ID NO: 4); amino acid 119 R-to-G (SEQ ID NO: 6), amino acid 175 T-to-I (SEQ ID NO: 8), and amino acid 232 N-to-S (SEQ ID NO: 10), all according to the human gene numbering. Alignment is based on reference sequences NP_037451.1 transitional epithelia response protein (*Homo sapiens*) (SEQ ID NO: 18); XP_514384.1PREDICTED: similar to transitional epithelia response protein (*Pan troglodytes*) (SEQ ID NO: 24); XP_001103913.1 PREDICTED: similar to transitional epithelia response protein (*Macaca mulatta*) (SEQ ID NO: 25); XP_544571.1 PREDICTED: similar to transitional epithelia response protein (*Canis familiaris*) (SEQ ID NO: 28); NP_082149.1 transitional epithelia response protein (*Mus musculus*) (SEQ ID NO: 26); XP_233672.1 PREDICTED: similar to transitional epithelia response protein (*Rattus norvegicus*) (SEQ ID NO: 27); XP_417615.1 PREDICTED: similar to transitional epithelia response protein (*Gallus gallus*) (SEQ ID NO: 29); NP_523581.1 heixuedian CG5876-PA (*Drosophila melanogaster*) (SEQ ID NO: 31); XP_317591.2 ENSANGP00000010121 (*Anopheles gambiae* str. PEST) (SEQ ID NO: 32).

FIG. 3. depicts the predicted UBIAD1 prenyltransferase domain-containing protein 1 structure from ModBase mapped with evolutionary conservation scores calculated by ConSurf. Five familial mutations plus one control variant detected in this study are indicated. a. Front view; b. Rear view.

BRIEF DESCRIPTION OF THE SEQUENCES

Figure 2:
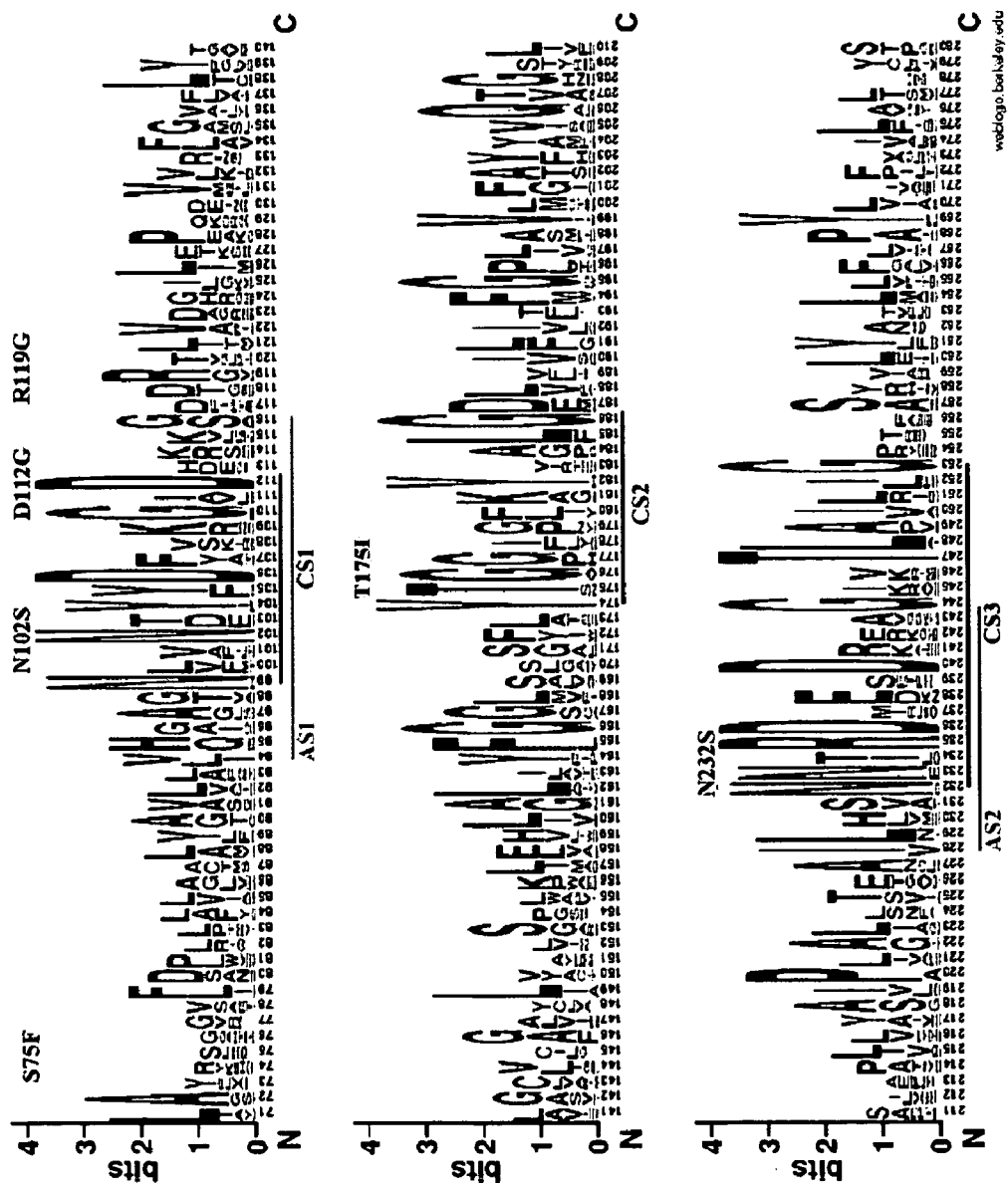
FIG. 2. depicts conserved amino acid residues in three regions of UBIAD1 containing familial mutations (CS1, CS2, CS3). Also shown are two regions aligning with putative bacterial UbiA active sites (AS1, AS2). Familial mutations plus the control variant detected in this study are highlighted above each consensus plot. The sequence logo was generated with the multiple sequence alignment of distant orthologs selected from Eukaryota, Bacteria, and Archaea.

Table 1 sets forth a brief description of the sequences listed herein.

TABLE 1

| SEQ ID # | Sequence |
|---|---|
| 1 | N102S DNA with non-coding region |
| 2 | N102S amino acid |
| 3 | D112G DNA with non-coding region |
| 4 | D112G amino acid |
| 5 | R119G DNA with non-coding region |
| 6 | R119G amino acid |
| 7 | T175I DNA with non-coding region |
| 8 | T175I amino acid |
| 9 | N232S DNA with non-coding region |
| 10 | N232S amino acid |
| 11 | S75F Polymorphism DNA with non-coding region |
| 12 | S75F Polymorphism amino acid |
| 13 | Active Site 1 DNA |
| 14 | Active Site 1 amino acid |
| 15 | Active Site 2 DNA |
| 16 | Active Site 2 amino acid |
| 17 | Wildtype DNA |
| 18 | Wildtype amino acid |
| 19 | N102S DNA |
| 20 | D112G DNA |
| 21 | R119G DNA |
| 22 | T175I DNA |
| 23 | N232S DNA |
| 24 | *Pan* amino acid - Wildtype |
| 25 | *Macaca* amino acid - Wildtype |
| 26 | *Mus* amino acid - Wildtype |
| 27 | *Rattus* amino acid - Wildtype |
| 28 | *Canis* amino acid - Wildtype |
| 29 | *Gallus* amino acid - Wildtype |
| 30 | *Xenopus* amino acid - Wildtype |
| 31 | *Drosophila* amino acid - Wildtype |
| 32 | *Anopheles* amino acid - Wildtype |
| 33 | Probe 1 - Active site 1 |
| 34 | Probe 2 - Active site 1 |
| 35 | Probe 3 - Active site 1 |
| 36 | Probe 4 - Active site 1 |
| 37 | Probe 5 - Active site 1 |
| 38 | Probe 6 - Active site 1 |
| 39 | Probe 7 - Active site 2 |
| 40 | Probe 8 - Active site 2 |
| 41 | Probe 9 - Active site 2 |
| 42 | Probe 10 - Active site 2 |
| 43 | Probe 11 - Active site 2 |
| 44 | Probe 12 - Active site 2 |
| 45 | Exon 1 left forward primer |
| 46 | Exon 1 left reverse primer |
| 47 | Exon 1 right forward primer |
| 48 | Exon 1 right reverse primer |
| 49 | Exon 2 left forward primer |
| 50 | Exon 2 left reverse primer |
| 51 | Exon 2 right forward primer |
| 52 | Exon 2 right reverse primer |
| 53 | Microsatellite primer 1 forward |
| 54 | Microsatellite primer 1 reverse |
| 55 | Microsatellite primer 2 forward |
| 56 | Microsatellite primer 2 reverse |
| 57 | Microsatellite primer 3 forward |
| 58 | Microsatellite primer 3 reverse |
| 59 | Microsatellite primer 4 forward |
| 60 | Microsatellite primer 4 reverse |
| 61 | Microsatellite primer 5 forward |
| 62 | Microsatellite primer 5 reverse |
| 63 | Microsatellite primer 6 forward |
| 64 | Microsatellite primer 6 reverse |
| 65 | Microsatellite primer 7 forward |
| 66 | Microsatellite primer 7 reverse |
| 67 | Microsatellite primer 8 forward |
| 68 | Microsatellite primer 8 reverse |
| 69 | Microsatellite primer 9 forward |
| 70 | Microsatellite primer 9 reverse |
| 71 | Microsatellite primer 10 forward |
| 72 | Microsatellite primer 10 reverse |
| 73 | Microsatellite primer 11 forward |
| 74 | Microsatellite primer 11 reverse |
| 74 | Microsatellite primer 12 forward |
| 76 | Microsatellite primer 12 reverse |
| 77 | Microsatellite primer 13 forward |

TABLE 1-continued

| SEQ ID # | Sequence |
|---|---|
| 78 | Microsatellite primer 13 reverse |
| 79 | Microsatellite primer 14 forward |
| 80 | Microsatellite primer 14 reverse |
| 81 | Microsatellite primer 15 forward |
| 82 | Microsatellite primer 15 reverse |
| 83 | Microsatellite primer 16 forward |
| 84 | Microsatellite primer 16 reverse |
| 85 | Microsatellite primer 17 forward |
| 86 | Microsatellite primer 17 reverse |
| 87 | Microsatellite primer 18 forward |
| 88 | Microsatellite primer 18 reverse |
| 89 | Microsatellite primer 19 forward |
| 90 | Microsatellite primer 19 reverse |
| 91 | Microsatellite primer 20 forward |
| 92 | Microsatellite primer 20 reverse |
| 93 | Microsatellite primer 21 forward |
| 94 | Microsatellite primer 21 reverse |
| 95 | Microsatellite primer 22 forward |
| 96 | Microsatellite primer 22 reverse |
| 97 | Microsatellite primer 23 forward |
| 98 | Microsatellite primer 23 reverse |
| 99 | Microsatellite primer 24 forward |
| 100 | Microsatellite primer 24 reverse |
| 101 | Microsatellite primer 25 forward |
| 102 | Microsatellite primer 25 reverse |
| 103 | Microsatellite primer 26 forward |
| 104 | Microsatellite primer 26 reverse |
| 105 | Microsatellite primer 27 forward |
| 106 | Microsatellite primer 27 reverse |
| 107 | Microsatellite primer 28 forward |
| 108 | Microsatellite primer 28 reverse |
| 109 | Microsatellite primer 29 forward |
| 110 | Microsatellite primer 29 reverse |
| 111 | Microsatellite primer 30 forward |
| 112 | Microsatellite primer 30 reverse |
| 113 | Microsatellite primer 31 forward |
| 114 | Microsatellite primer 31 reverse |
| 115 | Microsatellite primer 32 forward |
| 116 | Microsatellite primer 32 reverse |
| 117 | Microsatellite primer 33 forward |
| 118 | Microsatellite primer 33 reverse |
| 119 | Microsatellite primer 34 forward |
| 120 | Microsatellite primer 34 reverse |
| 121 | Microsatellite primer 35 forward |
| 122 | Microsatellite primer 35 reverse |

DETAILED DESCRIPTION

Definitions

The following definitions shall apply unless otherwise indicated.

The term "nucleic acid molecule", "nucleic acid sequence" or "polynucleotide" refers to any nucleic acid containing molecule, including but not limited to, DNA or RNA. The term polynucleotide(s) generally refers to any polyribonucleotide or polydeoxyribonucleotide, which may be unmodified DNA or RNA or modified DNA or RNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, "polynucleotide" as used herein refers to triple-stranded regions comprising DNA or RNA or both DNA and RNA. The strands in such regions may be from the same molecule or from different molecules. The regions may include all of one or more of the molecules, but more typically involve only a region of some of the molecules. One of the molecules of a triple-helical region often is an oligonucleotide.

The term "polynucleotide," "nucleic acid molecule" or "nucleic acid sequence" includes DNAs or RNAs that contain one or more modified bases. Thus, DNAs or RNAs with backbones modified for stability or for other reasons are "polynucloeotides," "nucleic acid molecules" or "nucleic acid sequences" as those terms are intended herein. The terms also encompass sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. The terms also encompass peptide nucleic acids, locked nucleic acids, cyclohexene nucleic acids, tricycle DNAs, phosphorthioate oligonucleotides, 2-O-methyl and 2-O-ethyl oligonucleotides, N3'-P5'-phosphoramidates, and morpholino oligonucloeotides.

It will be appreciated that a great variety of modifications have been made to DNA and RNA that serve many useful purposes known to those of skill in the art. The term "polynucleotide" as it is employed herein embraces such chemically, enzymatically or metabolically modified forms of polynucleotides, as well as the chemical forms of DNA and RNA characteristic of viruses and cells, including simple and complex cells, inter alia.

By "isolated nucleic acid sequence" is meant a polynucleotide that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double stranded forms of DNA.

The term "gene" refers to a nucleic acid (e.g., DNA) sequence that comprises coding sequences necessary for the production of a polypeptide, precursor or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment is retained. The term also encompasses the coding region of a structural gene and the sequences preceding and following the coding region, (leader and trailer) as well as intervening sequences (introns) between individual coding segments (exons). Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region (or upstream region) may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "oligonucleotide" as used herein is defined as a molecule comprised of two or more deoxyribonucleotides or ribonucleotides, preferably more than three, and usually more than ten. The exact size of an oligonucleotide will depend on many factors, including the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, Meth. Enzymol., 68:90-99; the phosphodiester method of Brown et al., 1979, Method Enzymol., 68:109-151, the diethylphosphoramidite method of Beaucage et al., 1981, Tetrahedron Lett., 22:1859-1862; the triester method of Matteucci et al., 1981, J. Am. Chem. Soc., 103:3185-3191, or automated synthesis methods; and the solid support method of U.S. Pat. No. 4,458,066.

The term "plasmid" generally is designated herein by a lower case p preceded and/or followed by capital letters and/ or numbers, in accordance with standard naming conventions that are familiar to those of skill in the art.

Plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The term "restriction endonucleases" and "restriction enzymes" refers to bacterial enzymes which cut double-stranded DNA at or near a specific nucleotide sequence.

As used herein, "vector" or "plasmid" refers to discrete elements that are used to introduce heterologous nucleic acids into cells for either expression or replication thereof. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art. An expression vector includes vectors capable of expressing DNA that is operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

A coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately produce the desired protein.

Nucleic acid sequences which encode a fusion protein of the invention can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, translational stop sites, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., *Methods in Enzymology* 153:516-544, 1987). For example, when cloning in bacterial systems, inducible promoters such as pL of bacteriophage y, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the nucleic acid sequences encoding a fusion protein of the invention may be inserted into a recombinant expression vector. The term "expression vector" refers to a plasmid, virus or other vehicle known in the art that has been manipulated by insertion or incorporation of the nucleic acid sequences encoding the fusion peptides of the invention. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene* 56:125, 1987), the pMSXND expression vector for expression in mammalian cells (Lee and Nathans, *J. Biol. Chem.* 263:3521, 1988), baculovirus-derived vectors for expression in insect cells, cauliflower mosaic virus, CaMV; and tobacco mosaic virus, TMV. The nucleic acid sequences encoding a fusion polypeptide of the invention can also include a localization sequence to direct the indicator to particular cellular sites by fusion to appropriate organellar targeting signals or localized host proteins. A polynucleotide encoding a localization sequence, or signal sequence, can be used as a repressor and thus can be ligated or fused at the 5' terminus of a polynucleotide encoding the reporter polypeptide such that the signal peptide is located at the amino terminal end of the resulting fusion polynucleotide/polypeptide. The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., 2001, and *Current Protocols in Molecular Biology*, M. Ausubel et al., eds., (Current Protocols, a joint venture between Greene Publishing Associates, Inc. and John Wiley & Sons, Inc., most recent Supplement). These methods include in vitro recombinant DNA techniques, synthetic techniques and in vivo recombination/genetic recombination. (See, for example, the techniques described in Sambrook, et al., *Molecular Cloning A Laboratory Manual*, Cold Spring Harbor Laboratory, N.Y., 2001).

Depending on the vector utilized, any of a number of suitable transcription and translation elements, including constitutive and inducible promoters, transcription enhancer elements, transcription terminators, etc. may be used in the expression vector (see, e.g., Bitter, et al., *Methods in Enzymology* 153:516-544, 1987). These elements are well known to one of skill in the art.

By "transformed cell" or "host cell" is meant a cell (e.g., prokaryotic or eukaryotic) into which (or into an ancestor of which) has been introduced, by means of recombinant DNA techniques, a DNA molecule encoding a polypeptide of the invention, or fragment thereof.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art. Eukaryotic cells can also be cotransfected with DNA sequences encoding a polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Preferably, a eukaryotic host is utilized as the host cell as described herein. The eukaryotic cell may be a yeast cell (e.g., *Saccharomyces cerevisiae*), or may be a mammalian cell, including a human cell.

A number of methods are used to transform yeast, including treatment with lithium salts, electroporation and transforming spheroplasts. See, e.g., *Current Protocols in Molecular Biology*, Ed. Ausubel, et al. (Supplements to 2005).

Eukaryotic systems, and mammalian expression systems, allow for proper post-translational modifications of expressed mammalian proteins to occur. Eukaryotic cells which possess the cellular machinery for proper processing of the primary transcript, glycosylation, phosphorylation, and, advantageous secretion of the gene product should be used. Such host cell lines may include but are not limited to yeast and fungal species and strains and eukaryotic cells such as CHO, VERO, BHK, HeLa, COS, MDCK, Jurkat, HEK-293, and WI38.

For long-term, high-yield production of recombinant proteins, stable expression is preferred. Rather than using expression vectors which contain viral origins of replication, host cells can be transformed with the cDNA encoding a fusion protein of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci, which in turn can be cloned and expanded into cell lines. For example, following the introduction of foreign DNA, engineered cells may be allowed to grow for 1-2 days in an enriched media, and then are switched to a selective media. A number of selection systems may be used, including, but not limited to the herpes simplex virus thymidine kinase (Wigler, et al., *Cell*, 11:223, 1977), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., *Cell,* 22:817, 1980) genes can be employed in tk⁻, hgprt⁻ or aprt⁻ cells respectively. Also, antimetabolite resistance can be used as the basis of selection for dhfr, which confers resistance to methotrexate (Wigler, et al., *Proc. Natl. Acad. Sci. USA* 77:3567, 1980; O'Hare, et al., *Proc. Natl. Acad. Sci. USA* 8:1527, 1981); gpt, which confers resistance to mycophenolic acid (Mulligan & Berg, *Proc. Natl. Acad. Sci. USA,* 78:2072, 1981; neo, which confers resistance to the aminoglycoside G-418 (Colberre-Garapin, et al., *J. Mol. Biol.* 150:1, 1981); and hygro, which confers resistance to hygromycin (Santerre, et al., *Gene* 30:147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047, 1988); and ODC (ornithine decarboxylase) which confers resistance to the ornithine decarboxylase inhibitor, 2-(difluoromethyl)-DL-ornithine, DFMO (McConlogue L., In: *Current Communications in Molecular Biology*, Cold Spring Harbor Laboratory, ed., 1987).

The terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" or "homologous" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid and is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. Likewise, a substantially complementary sequence or probe will compete for and inhibit the binding (i.e., the hybridization) of a completely complementary nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

The term "hybridizes" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization, 1985). Other references include more sophisticated computations that take structural as well as sequence characteristics into account for the calculation of $T_m$.

The term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology.

The term "isolated" means altered "by the hand of man" from its natural state; i.e., if it occurs in nature, it has been changed or removed from its original environment or both. For example, when used in relation to a nucleic acid, as in "an isolated nucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and antisense strands (i.e., the oligonucleotide or polynucleotide may be double-stranded).

As part of or following isolation, a polynucleotide can be joined to other polynucleotides, such as for example DNAs, for mutagenesis studies, to form fusion proteins, and for propagation or expression of the polynucleotide in a host. The isolated polynucleotides, alone or joined to other polynucleotides, such as vectors, can be introduced into host cells, in culture or in whole organisms. Such polynucleotides, when introduced into host cells in culture or in whole organisms, still would be isolated, as the term is used herein, because they would not be in their naturally occurring form or environment. Similarly, the polynucleotides and polypeptides may occur in a composition, such as a media formulation (solutions for introduction of polynucleotides or polypeptides, for example, into cells or compositions or solutions for chemical or enzymatic reactions which are not naturally occurring compositions) and, therein remain isolated polynucleotides or polypeptides within the meaning of that term as it is employed herein.

The term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used in connection with the present invention the term "polypeptide" or "protein" refers to a polymer in which the monomers are amino acid residues which are joined together through amide bonds. When the amino acids are alpha-amino acids, either the L-optical isomer or the D-optical isomer can be used, the L-isomers being preferred. The term "polypeptide" as used herein is intended to encompass any amino acid sequence and include modified sequences such as glycoproteins. The term "polypeptide" is specifically intended to cover naturally occurring proteins, as well as those which are recombinantly or synthetically synthesized, which occur in at least two different conformations wherein both conformations have the same or substantially the same amino acid sequence but have different three dimensional structures.

"Fragments" are a portion of a naturally occurring protein. Fragments can have the same or substantially the same amino acid sequence as the naturally occurring protein. "Substantially the same" or "Substantially similar" means that an amino acid sequence is largely, but not entirely, the same, but retains a functional activity of the sequence to which it is related. In general, two amino acid sequences are "substantially the same" or "substantially homologous" if they are at least 85% identical.

Amino acid substitutions, deletions and/or insertions, can be made. "Muteins" can be made by making conservative amino acid substitutions and also non-conservative amino acid substitutions. For example, amino acid substitutions that desirably or advantageously alter properties of the proteins can be made. In one embodiment, mutations that prevent degradation of the polypeptide can be made.

Amino acid substitutions contemplated include conservative substitutions, such as those set forth in Table 2. As described herein, substitutions that alter properties of the proteins are also contemplated.

Suitable conservative substitutions of amino acids are known to those of skill in this art and can be made generally without altering the biological activity, for example enzymatic activity, of the resulting molecule. Those of skill in this art recognize that, in general, single amino acid substitutions in non-essential regions of a polypeptide do not substantially alter biological activity (see, e.g., Watson et al. Molecular Biology of the Gene, 5th Edition, 2003, The Benjamin/Cummings Pub. Co.). Conservative amino acid substitutions are made, for example, in accordance with those set forth in Table 2.

TABLE 2

| Original Residue | Conservative Substitution |
| --- | --- |
| Ala (A) | Gly, Ser, Abu |
| Arg (R) | Lys, Orn |
| Asn (N) | Gln, His |
| Cys (C) | Ser |
| Gln (Q) | Asn |
| Glu (E) | Asp |
| Gly (G) | Ala, Pro |
| His (H) | Asn, Gln |
| Ile (I) | Leu, Val, Met, Nle, Nva |
| Leu (L) | Ile, Val, Met, Nle, Nv |
| Lys (K) | Arg, Gln, Glu |
| Met (M) | Leu, Tyr, Ile, Nle, Val |
| Ornithine | Lys, Arg |
| Phe (F) | Met, Leu, Tyr |
| Ser (S) | Thr |
| Thr (T) | Ser |
| Trp (W) | Tyr |
| Tyr (Y) | Trp, Phe |
| Val (V) | Ile, Leu, Met, Nle, Nv |

Other substitutions are also permissible and can be determined empirically or in accord with known conservative substitutions.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation, for example of possible modifications. The modified peptides can be chemically synthesized, or the isolated gene can be site-directed mutagenized, or a synthetic gene can be synthesized and expressed in bacteria, yeast, baculovirus, tissue culture and so on.

A DNA "coding sequence of" or a "nucleotide sequence encoding" a particular protein is a DNA sequence which is transcribed and translated into a protein when placed under the control of appropriate regulatory sequences.

"Amino acid sequence" and terms such as "polypeptide" or "protein" are not meant to limit the amino acid sequence to the complete, native amino acid sequence associated with the recited protein molecule.

A "recombinant" protein or polypeptide refers to proteins or polypeptides produced by recombinant DNA techniques; i.e., produced from cells transformed by an exogenous DNA construct encoding the desired polypeptide. "Synthetic" polypeptides are those prepared by chemical synthesis.

As used herein, the "regulatory region" of a gene is any part of a gene that regulates the expression of a gene, including, without limitation, transcriptional and translational regulation. The regions include without limitation the 5' and 3' regions of genes, binding sites for regulatory factors, including without limitation transcription factor binding sites. The regions also include regions that are as long as 20,000 or more base pairs upstream or downstream of translational start sites, so long as the region is involved in any way in the regulation of the expression of the gene. The region may be as short as 20 base pairs or as long as thousands of base pairs.

"UBIAD1" is likely an intrinsic membrane protein with a prenyltransferase functional domain. UbiA, the canonical family member, also known as 4-hydroxybenzoate octaprenyl transferase, catalyzes 1,4-dihydroxy-2-naphthoate→dimethylmenaquinone, in the ubiquinone biosynthetic pathway of bacteria (not to be confused with the UbiA gene in *C. elegans* which encodes ubiquitin and has no sequence homology to UBIAD1 or other genes in the family.)

The Role of UBIAD1 in Disease

Here we describe the identification of human gene UBIAD1 as causal for Schnyder Corneal Dystrophy. We analyzed two families of individuals affected by SCCD and discovered five mutated variants of the gene.

Analysis of a first Nova Scotia family (F1), containing 17 living affected individuals (F1), unilineally segregating SCCD revealed UBIAD1 as the defective gene responsible for this disorder. Initial microsatellite genotyping using markers from the published linkage interval on chromosome 1 were consistent with linkage in our family. Subsequent extensive fine mapping utilizing microsatellite markers were used to identified a shared haplotype, e.g., an interval from marker 10_55 to 11_85, containing the causal gene. This interval comprises approximately 3 cM of genetic distance, or 1.3 Mbp according to build 36, and contains 24 annotated genes from public databases.

A similar analysis of a second family (F2) with two lineally affected individuals identified an interval consistent with that in family F1. The two families together generated a multipoint sumLOD score of 8.7 using the 90% penetrance transmission model, with family F1 providing essentially all the statistical power.

Mutation detection by direct DNA sequencing was initiated across the 1.3 Mbp interval defined in family F1. Following tentative prioritization based on biological function, all or part of 9 genes were sequenced in three affected individuals. Approximately 125 distinct coding exons were sequenced in total, when potential causal variants were detected in both families in gene UBIAD1. NCBI sequence NP_037451.1 was used to define the reference full-length UBIAD1 coding region. In family F1, a missense variant aa119 R-to-G was identified, which segregated to all affected individuals in the pedigree consistent with being on the affected haplotype. In family F2, a missense variant aa175 T-to-I was identified, which segregated to the two affected individuals in the pedigree. Neither variant was detected in any unaffected individuals in the pedigree (including spouses), nor in a set of control samples collected from the local population (the exact number varies for each mutation due to sporadic sequence dropouts; the total number of potential controls is 150, equivalent to 300 chromosomes; sequencing is ongoing to complete the set). Neither variant occurs in dbSNP. UBIAD1 is highly conserved in vertebrates, and to a lesser extent in invertebrates (FIG. 1). All of the segregating missense variants in the families are in highly conserved residues. All five detected familial mutations occur in the prenyltransferase domain. Sequencing in controls did identify one further missense variation, amino acid 75 S-to-F. This variant was found in three separate controls, is in a residue not fully conserved across mammalian species, and may not have any causal effects. It is therefore the only additional reported nonsynonymous variant in UBIAD1 according to dbSNP (via the UCSC browser display).

DNA was obtained from from three additional unrelated pedigrees and sequencing of UBIAD1 for patients detected three additional missense variants, aa 102 N-to-S, aa 112 D-to-G, and aa 232 N-to-S, likewise in residues conserved across vertebrates and invertebrates (FIG. 1). These variants segregated appropriately with the disease state in their respective pedigrees. None of these variants was observed in control samples or in dbSNP. The identification of five different segregating, rare missense variants in an extremely conserved gene, support the identification of UBIAD1 as the causal gene for Schnyder crystalline corneal dystrophy.

There is extensive sequence divergence between human UBIAD 1 and *E. coli* UbiA; nonetheless ClustalW was able to align these two sequences. Direct conservation of mutated residues in our families is not evident across such a large evolutionary divide, but four of the five detected mutations lie near or within predicted active site regions of the bacterial enzyme based on molecular modeling (FIG. 2). This supports a deleterious effect of mutations in these regions of the protein.

No prenylation sites were predicted for UBIAD1 by PrePS. However, the same result was found for UbiA of *E. coli* K12, indicating that prenylation sites are not automatically found in prenyltransferases. PrePS did predict farnesyltransferase and geranylgeranyltransferase modification sites for human c-K-ras2 protein isoform a.

The role of putative prenyltransferases, or even prenyl binding proteins, in lipid or cholesterol metabolism is readily imagined. Prenyl condensation reactions are part of the basic biosynthetic pathway of cholesterol. The enzymes of this pathway are well understood; hence it seems unlikely that UBIAD1 plays such a direct role. However, prenyl binding proteins might play a role in regulating cholesterol biosynthesis; and UBIAD1 may be involved in modulating intracellular cholesterol levels. A corneal phenotype, similar to the opacity found in Schnyder patients, has been observed in other human genetic disorders of cholesterol transport, Niemann-Pick types A and C. Mutations in the Niemann-Pick C1 and C2 genes (NPC1, 2) cause abnormal intracellular cholesterol trafficking with excessive lysosomal accumulation. NPC1 contains a conserved sterol sensing domain, and NPC2 has been shown to bind cholesterol. Neither has obvious prenyl group binding activity, nor is either predicted to have a prenylation site by PrePS, but UBIAD1 might regulate their activities through an indirect mechanism. It should be recalled that Niemann-Pick diseases are typically recessive, involving mutations in both copies of the respective genes. Schnyder corneal dystrophy as clinically ascertained is dominant, and in fact none of the three mutations we have identified intrinsically generates a null phenotype. Individuals carrying more severe mutations in UBIAD1, or mutations in both copies of the gene, might have a different and more severe clinical phenotype yet to be ascertained. It has been found that administration of inhibitors of farnesyl transferase (a prenyltransferase) in humans has beneficial effects in diabetic retinopathy and macular degeneration.

The UBIAD1 gene was independently noted in expression studies in bladder and prostate cancer cells (the gene is called transient epithelial response (TERE1) in those studies) (McGarvey et al. *Oncogene* 20:1042-4051 (2001) and *Prostate* 54:144-155 (2003)). To date, the role of UB1AD1 gene/protein in bladder and prostate cancer is unknown. There is clear evidence of the role of prenylation (farnesyltransferase and geranylgeranyltransferase) of the cancer-associated proteins H-ras, K-rasA, K-rasB, N-ras, RhoA and RhoB. Inhibition of farnesyltransferase in mice that have tumors derived from H-ras-transformed cells leads to tumor regression. Also of interest is that McGarvey et al. reported that the UBIAD1 protein interacted with numerous ESTs of the XPG protein, a protein involved in nucleotide excision repair of DNA. Inefficient DNA repair is a hallmark of tumor initiation. Therefore, the commercial potential for therapies derived from targeting UB1AD1 may exceed just prostate and bladder cancer.

The predicted biochemical function of UB1AD1 is consistent with a role in cholesterol metabolism. To date, there is no literature investigating a role for UB1AD1 in cholesterol metabolism, except a reported protein interaction with apolioprotein E. However, the Niemann-Pick type C gene plays a role in regulating HDL-cholesterol levels in a mouse model, and the similarity in corneal phenotypes of NPC and SCCD suggests that UBIAD1 may function similarly. Once the specific biochemical function of UBIAD1 is defined, drug therapies may be realized to modulate serum cholesterol levels or flux. The mechanisms to target the UB1AD1 gene or protein will only be developed with a clearer understanding of the function of the protein, the regulation of the gene, and interactions with other proteins. UBIAD1 may also be a potential therapeutic target for some rare orphan diseases of lipid metabolism. Some examples of these diseases are: Niemann-Pick disease types A, B, C, D, abetalipoproteinemia, Gaucher disease, neutral lipid storage disease, and Tangier disease. Tangier Disease can be used as an example of interest. It is a rare autosomal recessive disorder of cholesterol metabolism, which is characterized by reduced levels of cholesterol and HDL. Clinical-features include the heavy deposition of cholesterol in each tonsil and, interestingly, retinitis pigmentosa. This is of interest considering that four prenyltransferase substates are the retinal cGMP phosphodiesterase a- and P-subunits, retinal transducin y-subunit and rhodopsin kinase.

Mutations are known in the putative Drosophila UBIAD1 ortholog heixuedian (heix). These exhibit an array of cellular and developmental phenotypes including abnormal imaginal disc growth, hemocyte overgrowth and melanotic tumors, and wing abnormalities. Other than P-element insertions, the molecular bases of heix alleles have not been reported, nor have subcellular histological examinations been reported. It will be interesting to examine heix mutants in the light of our results, to determine whether abnormal lipid transport or intracellular cholesterol deposition underly the developmental defects.

Nucleic Acid and Polypeptides

In one embodiment, the invention provides an isolated polynucleotide sequence encoding mutated UBIAD1 polypeptide. SEQ ID NOs 19, 20, 21, 22 and 23 are the complete open reading frame for UBIAD1 mutants. SEQ ID NO 11 includes the complete open reading frame for the UBIAD1 polymorphism. Exemplary UBIAD1 polypeptides of the invention have an amino acid sequence as set forth in SEQ ID NOs 2, 4, 6, 8, 10 and 12. Polynucleotide sequences of the invention include DNA, cDNA and RNA sequences which encode UBIAD1.

The invention also provides for fragments of the UBIAD1 nucleic acid sequence, including the sequences of the putative active sites of UBIAD1. SEQ ID NOs 13 and 15 encode the polypeptides of the putative active sites. The invention also includes DNA, cDNA and RNA sequences which encode UBIAD1 active sites.

The polynucleotides described and claimed here include naturally occurring, synthetic, and intentionally manipulated polynucleotides. For example, the UBIAD1 polynucleotide may be subjected to site-directed mutagenesis. The polynucleotides of the invention also include sequences that are degenerate as a result of the genetic code. There are 20 natural amino acids, most of which are specified by more than one codon. Therefore, all degenerate nucleotide sequences are included in the invention as long as the amino acid sequence of the polypeptide encoded by the nucleotide sequence is functionally unchanged. Also included are nucleotide sequences which encode UBIAD1 polypeptides, such as SEQ ID NOs 19, 20, 21, 22, 23 or 11. In addition, the invention also includes a polynucleotide encoding a polypeptide having the biological activity of an amino acid sequence of SEQ ID NOs 2, 4, 6, 8, 10 or 12. However, the invention also includes fragments of SEQ ID NOs 2, 4, 6, 8, 10, 11, 12, 19, 20, 21, 22 or 23. For example, fragments of SEQ ID NOs 19, 20, 21, 22, 23 or 11 at least 20 nucleotides in length as well as fragments of SEQ ID NOs 2, 4, 6, 8, 10 or 12 at least 7 amino acids in length are encompassed by the current invention, so long as they retain some biological activity related to the UBIAD1 polypeptide.

The polynucleotides of this invention were originally recovered from human DNA. Thus, the present invention provides a means for isolating similar nucleic acid molecules from other organisms, encoding polypeptides similar to the polypeptides of the present invention. For example, one may probe a gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 2005). It is appreciated by one skilled in the art that probes can be designed based on the degeneracy of the genetic code to the sequences set forth in SEQ ID NOs 2, 4, 6, 8, 10 or 12.

The invention includes polypeptides having substantially the same sequence as the amino acid sequence set forth in SEQ ID NOs 2, 4, 6, 8, 10 or 12 or functional fragments thereof, or amino acid sequences that are substantially the same as SEQ ID NOs 2, 4, 6, 8, 10 or 12. Thus, the invention includes the amino acid sequences of the modules of UBIAD1 set forth in SEQ ID NOs 14 and 16.

A protein having the amino acid sequence of the UBIAD1 protein to which one or more amino acid residues have been added is exemplified by a fusion protein containing the protein. Fusion proteins, in which the UBIAD1 protein is fused to other peptides or proteins, are included in the present invention. Fusion proteins can be made using techniques well known to those skilled in the art, for example, by linking the DNA encoding the UBIAD1 protein (SEQ ID NOs 2, 4, 6, 8, 10 or 12) in frame with the DNA encoding other peptides or proteins, followed by inserting the DNA into an expression vector and expressing it in a host. Alternatively, the chimeric sequence may be introduced into a host cell by homologous recombination. There is no restriction as to the peptides or proteins to be fused to the protein of the present invention.

For instance, known peptides which may be used for the fusion include the FLAG peptide (Hopp et al., BioTechnology 6:1204-1210, 1988), 6XHis that is made up of six histidine residues, 10× His, influenza hemagglutinin (HA), human c-myc fragment, VSV-GP fragment, p18HIV fragment, T7-tag, HSV-tag, E-tag, SV40 T antigen fragment, lck tag, alpha-tubulin fragment, B-tag, and Protein C fragment. Also, glutathione-S-transferase (GST), influenza hemagglutinin (HA), the constant region of immunoglobulin, beta-galactosidase, maltose binding protein (MBP), and the like may be used as a protein to be fused with the protein of this invention. Fusion proteins can be prepared by fusing the DNA encoding these peptides or proteins, which are commercially available, with the DNA encoding the protein of the invention, and expressing the fused DNA.

The proteins of the present invention may have variations in the amino acid sequence, molecular weight, isoelectric point, presence or absence of sugar chains, or form, depending on the cell or host used to produce them or the purification method utilized as described below. Nevertheless, so long as the protein obtained has a function equivalent to the UBIAD1 protein, it is within the scope of the present invention. For example, when the inventive protein is expressed in prokaryotic cells, e.g., E. coli, a methionine residue is added at the N-terminus of the original protein. The present invention also includes such proteins.

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Methods of alignment of sequence for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol* 48:443 (1970), by the search for similarity method of Person & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information. The BLAST algorithm also performs a statistical analysis of the similarity between two sequences (see, e.g., Karlin & Altschul, *Proc. Natl. Acad. Sci. USA* 90:5873 (1993)). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

The polynucleotide encoding UBIAD1 includes the nucleotide sequences of SEQ ID NOs 19, 20, 21, 22, 23, 11, 13 and 15, as well as nucleic acid sequences complementary to those sequences. When the sequence is RNA, the deoxyribonucleotides A, G, C, and T of SEQ ID NOs 19, 20, 21, 22, 23, 11, 13 and 15 are replaced by ribonucleotides A, G, C, and U, respectively. Also included in the invention are fragments (portions) of the above-described nucleic acid sequences that are at least 10 bases in length, which is sufficient to permit the fragment to selectively hybridize to DNA that encodes the protein of SEQ ID NOs 2, 4, 6, 8, 10, 12, 14, 16 or similar proteins. "Selective hybridization" as used herein refers to hybridization under moderately stringent or highly stringent physiological conditions (See, for example, the techniques described in Sambrook et al., 2001 Molecular Cloning A Laboratory Manual, Cold Spring Harbor Laboratory, New York, incorporated herein by reference), which distinguishes related from unrelated nucleotide sequences.

Also provided are nucleic acid molecules that hybridize to the above-noted sequences of nucleotides encoding UBIAD1 at least at low stringency, at moderate stringency, and/or at high stringency, and that encode one or part of one of the modules and/or the full length protein. Generally the molecules hybridize under such conditions along their full length (or along at least about 70%, 80% or 90% of the full length) for at least one domain or module and encode at least one domain, such as the condensation domain, of the polypeptide.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

Oligonucleotides encompassed by the present invention are also useful as primers for nucleic acid amplification reactions. In general, the primers used according to the method of the invention embrace oligonucleotides of sufficient length and appropriate sequence which provides specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acids of interest. Specifically, the term "primer" as used herein refers to a sequence comprising sixteen or more deoxyribonucleotides or ribonucleotides, preferably at least twenty, which sequence is capable of initiating synthesis of a primer extension product that is substantially complementary to a target nucleic acid strand. The oligonucleotide primer typically contains 15-22 or more nucleotides, although it may contain fewer nucleotides as long as the primer is of sufficient specificity to allow essentially only the amplification of the specifically desired target nucleotide sequence (i.e., the primer is substantially complementary).

Amplified products can be detected by Southern blot analysis, with or without using radioactive probes. In such a process, for example, a small sample of DNA containing a very low level of UBIAD1 nucleotide sequence is amplified and analyzed via a Southern blotting technique known to those of skill in the art. The use of non-radioactive probes or labels is facilitated by the high level of the amplified signal.

Plasmids, Vectors and Cells

Plasmids and vectors containing the nucleic acid molecules are also provided. Cells containing the vectors, including cells that express the encoded proteins are provided. The host cell can be prokaryotic or eukaryotic. The cell can be a bacterial cell, a yeast cell, including *Saccharomyces cerevisiae* or *Pichia pastoris*, a fungal cell, a plant cell, an insect cell or an animal cell. Methods for producing UBIAD1 or portions of the UBIAD1 polypeptide are provided herein. For example, growing the cell under conditions whereby the encoded UBIAD1 is expressed by the cell, and recovering the expressed protein, are provided.

DNA sequences encoding UBIAD1 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used.

In the present invention, the UBIAD1 polynucleotide sequences may be inserted into a recombinant expression vector. The term "expression vector" refers to a plasmid, virus or other vehicle known in the art that has been manipulated by insertion or incorporation of UBIAD1 nucleic acid sequences. Such expression vectors contain a promoter sequence which facilitates the efficient transcription of the inserted nucleic acid sequence of the host. The expression vector typically contains an origin of replication and a promoter, as well as specific genes which allow phenotypic selection of the transformed cells. Vectors suitable for use in the present invention include those described above.

Methods which are well known to those skilled in the art can be used to construct expression vectors containing the UBIAD1 coding sequence and appropriate transcriptional/translational control signals. These methods include in vitro recombinant DNA techniques, synthetic techniques, and in vivo recombination/genetic techniques. (See, for example, the techniques described in Sambrook et al., 2001, *Molecular Cloning a Laboratory Manual*, Cold Spring Harbor Laboratory, New York).

The genetic construct can be designed to provide additional benefits, such as, for example, the addition of C-terminal or N-terminal amino acid residues that would facilitate purification by trapping on columns or by use of antibodies. All of those methodologies are cumulative. For example, a synthetic gene can later be mutagenized. The choice as to the method of producing a particular construct can easily be made by one skilled in the art based on practical considerations: the size of the desired peptide, availability and cost of starting materials, etc. All of the technologies involved are well established and well known in the art. See, for example, Ausubel et al., *Current Protocols in Molecular Biology*, Volumes 1-4, with supplements 2005, and Sambrook et al., *Molecular Cloning, a Laboratory Manual*, Cold Spring Harbor Laboratory (2001). Yet, other technical references are known and easily accessible to one skilled in the art.

The UBIAD1 polypeptide and its domains, derivatives and analogs can be produced by various methods known in the art. For example, once a recombinant cell expressing a UBIAD1 protein, or a domain, fragment or derivative thereof, is identified, the individual gene product can be isolated and analyzed. This is achieved by assays based on the physical and/or functional properties of the protein, including, but not limited to, radioactive labeling of the product followed by analysis by gel electrophoresis, immunoassay or cross-linking to marker-labeled product.

The UBIAD1 polypeptides can be isolated and purified by standard methods known in the art, either from natural sources or recombinant host cells expressing the complexes or proteins. The methods include, but are not restricted to, column chromatography (e.g., ion exchange, affinity, gel exclusion, reversed-phase high pressure and fast protein liquid), differential centrifugation, differential solubility, or by any other standard technique used for the purification of proteins. Functional properties can be evaluated using any suitable assay known in the art.

Manipulations of UBIAD1 protein sequences can be made at the protein level. Also contemplated herein are UBIAD1 proteins, domains thereof, derivatives or analogs or fragments thereof, which are differentially modified during or after translation, e.g., by glycosylation, acetylation, phosphorylation, amidation, derivatization by known protecting/blocking groups, proteolytic cleavage or linkage to an antibody molecule or other cellular ligand. Any of numerous chemical modifications can be carried out by known techniques, including but not limited to, specific chemical cleavage by cyanogen bromide, trypsin, chymotrypsin, papain, V8 protease, $NaBH_4$, acetylation, formylation, oxidation, reduction and metabolic synthesis in the presence of tunicamycin.

A variety of modifications of the UBIAD1 protein and domains are contemplated herein. A UBIAD1-encoding nucleic acid molecule can be modified by any of numerous strategies known in the art Sambrook et al. (2001) Molecular Cloning: A Laboratory Manual (3rd Ed.), Vol. 1-3, Cold Spring Harbor Laboratory, Cold Spring Harbor, N.Y.). The sequences can be cleaved at appropriate sites with restriction endonuclease(s), followed by further enzymatic modification if desired, isolated and ligated in vitro. In the production of the gene encoding a domain, derivative or analog of UBIAD1, care should be taken to ensure that the modified gene retains the original translational reading frame, uninterrupted by translational stop signals, in the gene region where the desired activity is encoded.

Additionally, the UBIAD1-encoding nucleic acid molecules can be mutated in vitro or in vivo, to create and/or destroy translation, initiation, and/or termination sequences, or to create variations in coding regions and/or form new restriction endonuclease sites or destroy pre-existing ones, to facilitate further in vitro modification. Also, as described herein muteins with primary sequence alterations are contemplated. Such mutations can be effected by any technique for mutagenesis known in the art, including, but not limited to, chemical mutagenesis and in vitro site-directed mutagenesis (Hutchinson et al., J. Biol. Chem. 253:6551-6558 (1978)), use of TAB® linkers (Pharmacia). For example, a UBIAD1 protein or domain thereof can be modified to include a fluorescent label.

Antibodies

In another embodiment, the present invention provides antibodies that bind to UBIAD1 and to specific modules of UBIAD1 that may produce cyclic peptides similar to UBIAD1. Such antibodies are useful for research and diagnostic tools to identify organisms that express polypeptides similar to UBIAD1.

The term "epitope", as used herein, refers to an antigenic determinant on an antigen, such as a UBIAD1 polypeptide, to which the paratope of an antibody, such as a UBIAD1-specific antibody, binds. Antigenic determinants usually consist of chemically active surface groupings of molecules, such as amino acids or sugar side chains, and can have specific three-dimensional structural characteristics, as well as specific charge characteristics.

Procedures for producing antibodies are well known to those skilled in the art. The antibodies can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA) and tetanus toxoid. The coupled peptide is then used to immunize the animal (e.g., a mouse, a rat, a chicken or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, updated 2005, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

An antibody suitable for binding to UBIAD1 is specific for at least one portion of the UBIAD1 polypeptide (SEQ ID NOs 2, 4, 6, 8, 10, 12, 14 or 16). For example, one of skill in the art can use the peptides to generate appropriate antibodies of the invention. Antibodies of the invention include polyclonal antibodies, monoclonal antibodies and fragments of polyclonal and monoclonal antibodies.

The preparation of polyclonal antibodies is well-known to those skilled in the art. See, for example, Green et al., *Production of Polyclonal Antisera*, in *Immunochemical Protocols* (Manson, ed.), pages 1-5 (Humana Press 1992); Coligan et al., *Production of Polyclonal Antisera in Rabbits, Rats, Mice and Hamsters*, in *Current Protocols in Immunology*, including supplements, 2005., which are hereby incorporated by reference.

The preparation of monoclonal antibodies likewise is conventional and known to those skilled in the art. See, for example, Kohler & Milstein, *Nature*, 256:495 (1975); Coligan et al., sections 2.5.1-2.6.7; Harlow et al., *Antibodies: A Laboratory Manual*, page 726 (Cold Spring Harbor Pub. 1988), and Harlow, et al., *Using Antibodies: A Laboratory Manual* (Cold Spring Harbor Pub. 1999) which are hereby incorporated by reference.

Screening Assay for Modulators of Putative UBIAD1 Active Sites

In another embodiment, the invention provides a method for identifying a compound which modulates UBIAD1 expression or activity including incubating components comprising the compound and a UBIAD1 polypeptide, or a recombinant cell expressing a UBIAD1 polypeptide, under conditions sufficient to allow the components to interact and determining the affect of the compound on the expression or activity of the gene or polypeptide, respectively. The term "affect," as used herein, encompasses any means by which gene expression or protein activity can be modulated. Such compounds can include, for example, polypeptides, peptidomimetics, chemical compounds and biologic agents as described below.

Incubating includes conditions which allow contact between the test compound and UBIAD1, a cell expressing UBIAD1 or nucleic acid encoding UBIAD1. Contacting includes in solution and in solid phase. The test ligand(s)/compound may be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/-Technology*, 3:1008-1012, 1985), oligonucleotide ligation assays (OLAs) (Landegren, et al., *Science*, 241:1077, 1988), and the like. Molecular techniques for DNA analysis have been reviewed (Landegren, et al., *Science*, 242:229-237, 1988).

Thus, the method of the invention includes combinatorial chemistry methods for identifying chemical compounds that bind to UBIAD1 or affect UBIAD1 expression or activity. By providing for the production of large amounts of UBIAD1, one can identify ligands or substrates that bind to, modulate, affect the expression of or mimic the action of UBIAD1. For example, a polypeptide may have biological activity associated with the wild-type protein, or may have a loss of function mutation due to a point mutation in the coding sequence, substitution, insertion, deletion and scanning mutations.

A wide variety of assays may be used to screen for compounds that modulate UBIAD1 expression or activity, including labeled in vitro protein-protein binding assays, protein-DNA binding assays, electrophoretic mobility shift assays, immunoassays for protein binding, and the like. The purified protein may also be used for determination of three-dimensional crystal structure, which can be used for modeling intermolecular interactions, for example.

The term "agent" as used herein describes any molecule, e.g. protein or pharmaceutical, with the capability of altering or mimicking the physiological function or expression of UBIAD1. Generally, a plurality of assay mixtures is run in parallel with different agent concentrations to obtain a differential response to the various concentrations. Typically, one of these concentrations serves as a negative control, i.e. at zero concentration or below the level of detection.

Candidate agents encompass numerous chemical classes, including organic molecules, preferably small organic compounds having a molecular weight of more than 50 and less than about 2,500 daltons. Candidate agents may comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification and amidification to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and anti-digoxin. For the specific binding members, the complementary member would normally be labeled with a molecule that provides for detection, in accordance with known procedures.

A variety of other reagents may be included in the screening assay. These include reagents like salts, neutral proteins, e.g., albumin, detergents, etc. that are used to facilitate optimal protein-protein binding and/or reduce non-specific or background interactions. Reagents that improve the efficiency of the assay, such as protease inhibitors, nuclease inhibitors and anti-microbial agents may be used. The mixtures of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hour will be sufficient.

EXAMPLES

Example 1

Microsatellite genotyping was performed using fluorescent primers set forth in Table 3. 5' tags were added to the reverse, unlabelled primer in each case to reduce variable non-templated nucleotide addition. Products were resolved on ABI 377 electrophoresis instruments and genotype chromatograms were interpreted using the GeneMarker program from SoftGenetics, Inc.

TABLE 3

| SEQ ID | For/Rev | Primers | Size |
|---|---|---|---|
| 53 | F | FAM-CAACTCATTTCCAGGGCTTT | 241 |
| 54 | R | GTTTCTTGTGGTCCATAGACCCCACAG | |
| 55 | F | HEX-CACACCTTTCCTTCGTCCAT | 277 |
| 56 | R | GTTTCTTTTCAAGGGGGTAGTAGGGAGT | |
| 57 | F | NED-AAGTCTGGACACTCCCCTGA | 299 |
| 58 | R | GTTTCTTTAAGGCCAGCAGTCCTCATC | |
| 59 | F | FAM-TGGGAGAGAGAGAATGAATGTG | 132 |
| 60 | R | GTTTCTTGAGGTCGAAGGGAAAAGAGG | |
| 61 | F | HEX-TCTCCTTGCTGCCCTAGTTT | 151 |
| 62 | R | GTTTCTTCTCCTTTCCCCCATGTCAG | |
| 63 | F | NED-TTGGGGCAAATACAATGAAAA | 180 |
| 64 | R | GTTTCTTTTCCTCACCATCCTTTCCTG | |
| 65 | F | /5HEX/ACTAACTTGTCCCAGATTACTGTGT | 117 |
| 66 | R | GTTTCTTGGCAACAAAGGGAGACTCTG | |

TABLE 3-continued

| SEQ ID | For/Rev | Primers | Size |
|---|---|---|---|
| 67 | F | /56-FAM/CGGTGGAATTTAGAAGCCTATG | 145 |
| 68 | R | GTTTCTTCCTGAATGATGTTCCCTTTCA | |
| 69 | F | FAM-TCGCAAGTAGAAGGTTTTGGA | 257 |
| 70 | R | GTTTCTTTGCACCACTAGGAGGCTACA | |
| 71 | F | NED-GTGGGAGGATTGCTTGAGG | 180 |
| 72 | R | GTTTCTTTGCTTAGCAAAAGCTATCCAAA | |
| 73 | F | /5HEX/ACCTAGCAGGCGGAGGTT | 195 |
| 74 | R | GTTTCTTTGGTGATACTAAAAACTGTATGCAAAG | |
| 75 | F | /56-FAM/CATGTGGCCTAACAAAAGG | 214 |
| 76 | R | GTTTCTTAAAAACAAAGGTGCCTGGTG | |
| 77 | F | NED-CAGGGAGCTCTGTGTTTGAA | 250 |
| 78 | R | GTTTCTTACCTAATGAACGGGCAACAG | |
| 79 | F | HEX-AATCTCTGTTCCCCAGCAAC | 276 |
| 80 | R | GTTTCTTGGGCAGCCTGACATACCTAC | |
| 81 | F | /5HEX/CGGGGAAATCCAATACGCTGAA | 270 |
| 82 | R | GTTTCTTCCGTCTCTCTTGCTGTCCTC | |
| 83 | F | /56-FAM/ATGTCCGGGAATCAACACAC | 292 |
| 84 | R | GTTTCTTGAACTGCCCTGGAATGAACT | |
| 85 | F | NED-TCCCCAAAACTCTCTCCTCA | 292 |
| 86 | R | GTTTCTTCAGGACCTCACAGCTCTTGG | |
| 87 | F | /5HEX/AGGACCTGACCCTGAGACCT | 116 |
| 88 | R | GTTTCTTAGCTCTGAGCCATTCGAGAG | |
| 89 | F | /56-FAM/TGTCTGTCCAACAAGAAGATGC | 145 |
| 90 | R | GTTTCTTATTGAAGCCAGGCTGAGAGG | |
| 91 | F | FAM-TTCAGCATCATGTGGTTTGG | 145 |
| 92 | R | GTTTCTTTTTCCCCTATGTGACAGCATC | |
| 93 | F | NED-TGTTGACTGTCTGGCCATCT | 180 |
| 94 | R | GTTTCTTAGGGCTCAGAGAGGAGCTGT | |
| 95 | F | /5HEX/TTATCCCACCGCTTTCTCTG | 205 |
| 96 | R | GTTTCTTGAAATGGAGGAGGGGAAAAT | |
| 97 | F | HEX-CAGACTCCCAAGCACAGACA | 164 |
| 98 | R | GTTTCTTGTCCCCTGGCAGGTGTAGTA | |
| 99 | F | /5HEX/CCAGCGCTGTACCTAAGCTG | 121 |
| 100 | R | GTTTCTTCCACTTGGGTGTCTGTGCAT | |
| 101 | F | /56-FAM/CAAACAAGACCCCAAACCAG | 230 |
| 102 | R | GTTTCTTGGGGGTGAGTAGCTCTTCTG | |
| 103 | F | /56-FAM/CAAACAAGACCCCAAACCAG | 177 |
| 104 | R | GTTTCTTGCTCAGAGAGGGGTCTGAACT | |
| 105 | F | /5HEX/CCAGGACCTCCTGACTTGAC | 244 |

TABLE 3-continued

| SEQ ID | For/Rev Primers | Size |
|---|---|---|
| 106R | GTTTCTTCTGCTAGGCTGGATGCTACA | |
| 107F | /56-FAM/AGACTCCCAGGGTCGTCAG | 298 |
| 108R | GTTTCTTGAGGTCGCTCCTGGATGTAG | |
| 109F | NED-CGGTCTGAGAAGCTTCAGG | 253 |
| 110R | GTTTCTTCAGAAAGTGCGCAGAGTGG | |
| 111F | /5HEX/TGGTTCTCATATACCTGCTTTGC | 136 |
| 112R | GTTTCTTGCTGGGCGACAGAGCTA | |
| 113F | /56-FAM/AGAAGTTTCGGTGAGCCAAG | 177 |
| 114R | GTTTCTTCTCCTCACTGGCTTGGAAAC | |
| 115F | /56-FAM/ACCTTCAGCTTCGGTCTCCT | 292 |
| 116R | GTTTCTTGTGAGGGTGGAGAGTTCAGC | |
| 117F | /5HEX/TGGGTGGGTAAGGGCTGTGTAA | 282 |
| 118R | GTTTCTTGGTGCTGGTTGATGAATCCT | |
| 119F | NED-CACCTGCATAGGGCCATC | 186 |
| 120R | GTTTCTTCCCTCCCTCTGTTAACCATGT | |
| 121F | /56-FAM/TGCTGGAGTTCAAGAGCCTGT | 306 |
| 122R | GTTTCTTGGCCTCACTACCTGAACCTG | |

Example 2

Pedigree files and genotype data were imported into Progeny Lab software version (6.6.01). Mendelian inconsistencies were identified with Pedcheck version 1.1. Allele calls for inconsistent markers were set to 0 in the offending nuclear families involved in the inconsistencies. Genetic positions from the Decode map were used when available. To calculate genetic position for markers not on the Decode map, linear interpolation was used between the two closest common markers flanking the markers to position, using physical distances provided by human genome assembly build 36.

Example 3

Two-point linkage was carried out using the MLINK routine of FASTLINK v4.1P on Linux. LOD scores were compiled by extracting results from the final.out output file using MLINK_LODS v2. Multipoint linkage analysis and haplotyping were carried out using SIMWALK version 2.90 on Linux. The input files were converted to SIMWALK format using Mega2 v3.0 R4. The haplotype routine converged on the first run for both pedigrees.

Example 4

Statistical Analyses were Conducted with Two Models

1. An affected only model in which all unaffected individuals except spouses were set to unknown and using penetrance set to 0.99, phenocopy rate set to 0.001 for a dominant disease with allele frequency of 0.001.

2. Penetrance set to 0.90 with a phenocopy rate of 0.001 and a dominant disease allele frequency of 0.001.

Example 5

Marker allele frequencies were estimated by maximum likelihood using Merlin version 1.0.1 (option-fm). As Merlin cannot handle large pedigrees, pedigree 1 was divided into three smaller families (branch 2/3, 74/75 and 100/103/101) for this stage of the analysis. Allelic frequencies from Merlin were manually incorporated into dat files.

Example 6

For mutation detection, protein coding regions of genes were amplified using primers designed with Primer3 and set forth in Table 4, from affected individuals 1349 and 1432 from family F1 and affected individual 1419 from family F2. Coding exons of gene UBIAD1 were subsequently sequenced in samples from additional affected individuals in all five families, and from a set of Nova Scotia population controls. PCR products were sequenced using ABI 377 electrophoresis instruments. Sequence chromatograms were interpreted using the MutationSurveyor program from SoftGenetics, Inc., with gene annotations from GenBank.

TABLE 4

| Exon 1 Left | F: CGG AAC CGA AGG AAG GTC | SEQ ID 45 |
|---|---|---|
| | R: CCA AGA TTC GGT CCA CAA GT | SEQ ID 46 |
| Exon 1 Right | F: GGC TCT TGG TGG GTT GTG | SEQ ID 47 |
| | R: AAA GCG GCT TAA ATT AGA AAG C | SEQ ID 48 |
| Exon 2 Left | F: AAG TGG CCT GCC TCT TCA C | SEQ ID 49 |
| | R: GCT GAT GGT GCA GTG TGT G | SEQ ID 50 |
| Exon 2 Right | F: GGG AGG CTG GTA TCG TCA C | SEQ ID 51 |
| | R: TGA CTG CCA AAT CAC ATT CC | SEQ ID 52 |

Example 7

InterPro, Pfam, ProSite, PSORTII, HMMTOP, TMPRED, TOPPRED, TMM, SignalP, MITOPROT, PTS1, bigPI, DGPI, NMT, PESTfind and PrePS were run via the Expasy web site. The effects of amino acid substitutions on protein function were predicted with SIFT, PolyPhen, and PANTHER. Homologous peptide sequences of human UBIAD1 gene in Eukaryota, Archaea and Bacteria were retrieved from NCBI genome database with BLAST. Multiple sequence alignments were computed by ClustalW and displayed with BoxShade. The sequences of distantly related orthologs were aligned by MUSCLE. The sequence logo was created by WebLogo. The evolutionary conservation of amino acid sites with mutations was analyzed using ConSurf. The predicted protein structure from ModBase for the UbiA prenyltransferase domain-containing protein 1 was used to build a 3D model. FIG. 3 was generated using PyMOL.

Example 8

Three tools, SIFT, PANTHER and POLYPHEN were employed to judge the potential pathogenicity of the five familial plus one control missense variant. The familial variants are predicted to have pathogenic consequences on the protein whereas the control variant S75F is predicted to be benign. All three methods predicted the familial mutations D112G and T175I have deleterious effects on protein function. Two out of three methods predicted that the other three familial variants N102S, R119G, N232S have damaging effects.

Table 5. Effects of mutations predicted by SIFT, PANTHER and PolyPhen. Sequence homology for SIFT prediction was calculated with the alignment of orthologs selected from Eukaryota. '−' and '+' indicate the predicted benign and deleterious effects of the mutations, respectively.

TABLE 5

| Mutation | Method | | |
|---|---|---|---|
| | SIFT | PANTHER | PolyPhen |
| S75F | − | − | − |
| N102S | + | + | − |
| D112G | + | + | + |
| R119G | + | − | + |
| T175I | + | + | + |
| N232S | + | − | + |

Example 9

The evolutionary conservation score for each residue of UBIAD1 was calculated and mapped to a predicted 3-dimensional protein structure by ConSurf (FIG. 3). The scores for the 5 residues with familial missense mutations, e.g. N102, D112, R119, T175, and N232 are 9, 9, 7, 9, and 9, respectively. The score for residue S75 with mutation in control sample is 1. All five residues with mutations detected in patients are highly evolutionary conserved in comparison to the variant of the control sample. The familial variants also locate close to each other in contrast to the control variant on the predicted protein structure model. Structurally and functionally important regions in the protein typically appear as patches of evolutionarily conserved residues that are spatially close to each other. The evolutionary conservation and the physical proximities of the five familial variants support that the variants are in a functional region of UBIAD1 protein.

What is claimed is:

1. An isolated nucleic acid molecule comprising a sequence that encodes the polypeptide comprising SEQ ID NO: 2.

2. The isolated nucleic acid molecule of claim 1, wherein the polypeptide consists essentially of SEQ ID NO: 2.

3. The isolated nucleic acid molecule of claim 1, wherein the polypeptide consists of SEQ ID NO: 2.

4. The isolated nucleic acid molecule of claim 1, wherein said nucleic acid molecule is DNA.

5. The isolated nucleic acid molecule of claim 1, wherein said nucleic acid molecule is RNA.

6. An isolated nucleic acid molecule comprising SEQ ID NO: 19.

7. The isolated nucleic acid molecule of claim 6 consisting essentially of SEQ ID NO: 19.

8. The isolated nucleic acid molecule of claim 6 consisting of SEQ ID NO: 19.

9. An expression vector comprising the nucleic acid molecule of claim 1.

10. The expression vector of claim 9, wherein said nucleic acid molecule comprises the sequence of SEQ ID NO: 19.

11. The expression vector of claim 9, wherein said vector is a plasmid or a viral particle.

12. The expression vector of claim 9, wherein said nucleic acid molecule is operably linked to an expression control sequence.

13. A host cell comprising the vector of claim 9.

14. A composition comprising the nucleic acid molecule of claim 1 and an acceptable carrier or diluent.

15. A composition comprising the expression vector of claim 9 and an acceptable carrier or diluent.

* * * * *